(12) United States Patent
Ishii et al.

(10) Patent No.: US 7,347,986 B2
(45) Date of Patent: Mar. 25, 2008

(54) SILICA-COATED MIXED CRYSTAL OXIDE PARTICLE, PRODUCTION PROCESS THEREOF AND COSMETIC MATERIAL USING THE SAME

(75) Inventors: Nobuaki Ishii, Kawasaki (JP); Kouichi Wada, Kawasaki (JP); Michihiro Takama, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 718 days.

(21) Appl. No.: 10/489,407

(22) PCT Filed: Sep. 13, 2002

(86) PCT No.: PCT/JP02/09432

§ 371 (c)(1),
(2), (4) Date: Mar. 12, 2004

(87) PCT Pub. No.: WO03/025071

PCT Pub. Date: Mar. 27, 2003

(65) Prior Publication Data

US 2004/0241189 A1 Dec. 2, 2004

Related U.S. Application Data

(60) Provisional application No. 60/368,967, filed on Apr. 2, 2002.

(30) Foreign Application Priority Data

Sep. 14, 2001 (JP) .............................. 2001-280147

(51) Int. Cl.
*A61Q 17/04* (2006.01)
*A61Q 17/00* (2006.01)
*A61Q 19/04* (2006.01)
*A61Q 19/00* (2006.01)
*A61K 8/02* (2006.01)

(52) U.S. Cl. .......................... 424/59; 424/60; 424/400; 424/401

(58) Field of Classification Search ............. 424/200.1, 424/59, 60, 400, 401
See application file for complete search history.

(56) References Cited

U.S. PATENT DOCUMENTS

| | | | |
|---|---|---|---|
| 3,640,744 A | | 2/1972 | Dietz et al. |
| 5,902,569 A | * | 5/1999 | Oshima et al. ............... 424/59 |
| 6,235,270 B1 | * | 5/2001 | Ishii et al. ..................... 424/59 |
| 6,572,964 B2 | * | 6/2003 | Tanaka et al. .............. 428/328 |
| 2001/0014396 A1 | | 8/2001 | Tanaka et al. |

OTHER PUBLICATIONS

C. J. Brinker, Sol-Gel Science, pp. 581-583, Academic Press, 1990.
"Silicic acid", Kagaku Daijiten (Chemical Dictionary, 7th Printing), Mar. 15, 1969.
"Funtai (Particles)", pp. 56-66, 1979.
"Cosmetic Material Standard, 2nd Edition, Annotated", Nihon Koteisho Kyokai, 1984.
"Cosmetic Material Standards: Standardized Mixing Components", Ministry of Health and Welfare, Pharmaceutical Affairs Department, 1993.
Supplementary Cosmetic Material Standards: Standardized Mixing Components, Ministry of Health and Welfare, Pharmaceutical Affairs Department, 1993.
"Cosmetic Classification and Approval Standards", Ministry of Health and Welfare, Pharmaceutical Affairs Department, 1993.
"Encyclopedia of Cosmetic Material Terms", Nikko Chemicals, 1996.
Seino, M., "Titanium Oxide . . . Properties and Application Techniques", pp. 196-197, 1991.

* cited by examiner

*Primary Examiner*—Shelley A. Dodson
(74) *Attorney, Agent, or Firm*—Sughrue Mion, PLLC

(57) ABSTRACT

Provided are a silica-coated mixed crystal oxide particle which has high dispersibility, excellent visible light transparency and superior ultraviolet-shielding capability and which is sufficiently reduced in the photocatalytic activity; an economical production process thereof; and an ultraviolet-shielding cosmetic material containing the silica-coated mixed crystal oxide particle, which is particularly excellent in the visible light transparency. The surface of a mixed crystal oxide particle having a BET specific surface area of 10 to 200 $m^2/g$ and containing primary particles in a mixed crystal is covered with a dense and thin film silica.

27 Claims, No Drawings

SILICA-COATED MIXED CRYSTAL OXIDE PARTICLE, PRODUCTION PROCESS THEREOF AND COSMETIC MATERIAL USING THE SAME

CROSS-REFERENCE TO RELATED APPLICATIONS

This application claims the benefit pursuant to 35 U.S.C. §119(e) (1) of U.S. Provisional Application, No. 60/368,967 filed Apr. 2, 2002.

TECHNICAL FIELD

The present invention relates to a silica-coated mixed crystal oxide particle obtained by coating a dense and practical silica thin film having a specific infrared absorption spectrum peak on the surface of a mixed crystal oxide particle having a BET specific surface area of 10 to 200 $m^2/g$ and containing primary particles in a mixed crystal state, which has good dispersibility and is suitably used for cosmetic materials, particularly ultraviolet-shielding cosmetic materials, and also relates to a production process thereof. Furthermore, the present invention relates to a cosmetic material containing the silica-coated mixed crystal oxide particle, which exhibits good feeling on use at the making up, excellent effect of preventing unpleasant whitening, high ultraviolet-shielding capability and good storage stability.

BACKGROUND ART

For ultraviolet-shielding cosmetic materials, a metal oxide such as titanium oxide, zinc oxide or cerium oxide is widely used as an inorganic ultraviolet-shielding material having excellent ultraviolet-shielding capability and high safety.

However, if such a metal oxide is blended as it is in a cosmetic material, there arise problems such as uncomfortable feeling on use or adverse effect on the human body due to photocatalytic activity of the metal oxide. Accordingly, the metal oxide surface is covered with an inorganic substance having no photocatalytic activity. Metal oxides covered with alumina or silica are commercially available but a product satisfied in both the inhibition of photocatalytic activity by coating and good use feeling when blended in a cosmetic material, is not known.

The present inventors have previously disclosed a silica-coated metal oxide having a silica film where the ratio I of the absorption peak intensity at from 1,150 to 1,250 $cm^{-1}$ to the absorption peak intensity at from 1,000 to 1,100 $cm^{-1}$ on the infrared absorption spectrum ($I=I_1/I_2$, wherein $I_1$ is a maximum absorption peak intensity in the range of 1,150 to 1,250 $cm^{-1}$ and $I_2$ is a maximum absorption peak intensity in the range of 1,000 to 1,100 $cm^{-1}$) is 0.2 or more and the refractive index is 1.435 or more; a production process thereof; and a cosmetic material containing the silica-coated metal oxide. Also, it has been verified that an ultraviolet-shielding cosmetic material ensuring good use feeling, high effect of preventing photocatalytic activity and excellent storage stability can be obtained by containing the above-described silica-coated metal oxide where a silica film is coated to a film thickness of 0.1 to 100 nm and the photocatalytic activity determined by a tetralin auto-oxidation method is 60 Pa/min or less.

In recent years, the ultraviolet-shielding cosmetic material is required to have good use feeling or high transparency in addition to high ultraviolet-shielding capability. Accordingly, the metal oxide used as an ultraviolet-shielding material is also demanded to have a primary particle size smaller than conventional materials and have excellent dispersibility so as to give good use feeling or high transparency when blended in a cosmetic material. The above-described silica-coated metal oxide previously proposed by the present inventors has excellent properties such as inhibition of photocatalytic activity and good use feeling but in order to elevate the transparency on blending in a cosmetic material, production of finer particles and improvement of dispersibility are in need of improvement.

However, a metal oxide powder having a small primary particle size is difficult to highly disperse because if it is suspended in a solvent, aggregation takes place. Therefore, before the coating with silica or during the silica coating reaction, an extra step such as ultrasonic dispersion treatment or cracking treatment by wet beads mill, homogenizer or the like is necessary and this is a problem in view of profitability.

DISCLOSURE OF INVENTION

The object of the present invention is to provide a silica-coated mixed crystal oxide particle having high dispersibility, excellent visible light transparency and superior ultraviolet-shielding capability and being sufficiently reduced in the photocatalytic activity; an economical production process thereof; and an ultraviolet-shielding cosmetic material containing the silica-coated mixed crystal oxide particle, which is particularly excellent in the visible light transparency.

Under these circumstances, the present inventors have made extensive investigations and found a silica-coated mixed crystal oxide particle having further excellent dispersibility and being suitable for use in cosmetic materials, particularly ultraviolet-shielding cosmetic materials excellent in the visible light transparency (first object), and a production process thereof (second object), where a dense and practical silica thin film having a specific infrared absorption spectrum peak is coated on the surface of a mixed crystal oxide particle having a BET specific surface area of 10 to 200 $m^2/g$ and containing primary particles in a mixed crystal state.

It is also found that the cosmetic material having blended therein the above-described silica-coated mixed crystal oxide particles exhibits good use feeling and high transparency at the making up, high ultraviolet-shielding capability and excellent storage stability (third object).

In order to attain the first object of the present invention, the present invention provides a silica-coated mixed crystal oxide particle obtained by covering the surface of a silica-coated mixed crystal oxide particle with a practical and dense silica film having a specific absorption peak ratio on an infrared absorption spectrum, good conformability to a complicated shape of the mixed crystal oxide particle, and good covering property even with an extremely small film thickness.

The term "dense" as used herein means that the silica film formed has a refractive index of 1.435 or more. In general, the denseness and the refractive index of a silica film have a positive correlation (see, for example, C. JEFFEREY BRINKER, Saul-GEL SCIENCE, 581 to 583, ACADEMIC PRESS (1990)). The refractive index of silica film obtained by a conventional sol-gel method is, if burnt, 1.435 or more, but if not burnt, less than 1.435 and the denseness is low. In the present invention, this value is achieved without performing the burning.

The term "practical" as used herein means that the covering power of silica to the substrate is strong to cause substantially no stripping of the coating and the silica film has an appropriate hydrophilicity. The hydrophilicity of silica film is expressed by the ratio I of the absorption peak intensity at from 1,150 to 1,250 cm$^{-1}$ to the absorption peak intensity at from 1,000 to 1,100 cm$^{-1}$ on the infrared absorption spectrum (I=$I_1/I_2$, wherein $I_1$ represents a maximum absorption peak intensity in the range of 1,150 to 1,250 cm$^{-1}$ and $I_2$ represents a maximum absorption peak intensity in the range of 1,000 to 1,100 cm$^{-1}$).

More specifically, $I_1$ is an absorption attributable to the deformation vibration of SiOH, $I_2$ is an absorption attributable to the stretching vibration of Si—O—Si and as the $I_1/I_2$ value is larger, the hydrophilicity is higher. The term "appropriate hydrophilicity" as used in the present invention means that this I value is 0.2 or more. The I value of silica film obtained by a conventional sol-gel method is, if not burnt, 0.2 or more, however, the denseness decreases as described above. On the other hand, if burnt, although the denseness is improved, the I value becomes less than 0.2 and the hydrophilicity decreases to fail in having an appropriate hydrophilicity.

As such, the silica film of the present invention has an appropriate hydrophilicity and therefore, maintains good surface physical properties (wet feeling and lubricity) when blended in a cosmetic material. At the same time, the film is a dense and strong coating which has not been obtained unless burnt. Therefore, even in the case of an extremely small thickness of about 0.1 nm, the coating can maintain high capability of preventing the photocatalytic activity of the mixed oxide particle.

In order to attain the second object of the present invention, the present invention provides a production process of a silica-coated mixed crystal oxide particle, comprising adding, in any order, a) a silicic acid or a precursor capable of producing a silicic acid, b) an alkali, c) an organic solvent and if desired, d) water to a mixed crystal oxide particle having a BET specific surface area of 10 to 200 m$^2$/g and containing primary particles in a mixed crystal state, such that the water/organic solvent ratio after the addition is from 0.1 to 10 and the silicon concentration is from 0.0001 to 5 mol/l, thereby depositing silica on the surface of the mixed crystal oxide particle to form a silica film.

In order to attain the third object of the present invention, it has been found that a cosmetic material having desired properties can be obtained by blending a silica-coated mixed crystal oxide particle where the surface of a mixed crystal oxide particle is covered with silica having a silica film thickness of 0.1 to 25 nm. The third aspect of the present invention has been accomplished based on this finding.

That is, the third aspect of the present invention is to provide a cosmetic material containing a mixed crystal oxide particle having a BET specific surface area of 10 to 200 m$^2$/g and containing primary particles in a mixed crystal state.

Also, the third aspect of the present invention is to provide the above-described cosmetic material containing a silica-coated mixed crystal oxide particle having a silica film thickness of 0.1 to 25 nm, wherein the photocatalytic activity of the silica-coated mixed crystal oxide particle determined by a tetralin auto-oxidation method is 60 Pa/min or less, preferably 45 Pa/min or less, the dye discoloration rate ($\Delta ABS_{490}$/hr) of the silica-coated mixed crystal oxide particle determined by a Sunset Yellow method is 0.1 or less, preferably 0.06 or less, and the kinetic friction coefficient of the silica-coated mixed crystal oxide particle determined by a glass plate method is 0.550 or less, preferably 0.500 or less.

Furthermore, the third aspect of the present invention is to provide the above-described cosmetic material which contains an antioxidant substance, and the above-described cosmetic material which further contains an ultraviolet absorber.

More specifically, the present invention relates to the following matters.

(1) A silica-coated mixed crystal oxide particle, wherein the surface of a mixed crystal oxide particle having a BET specific surface area of 10 to 200 m$^2$/g and containing primary particles in a mixed crystal is covered with a dense and thin film silica.

(2) The silica-coated mixed crystal oxide particle as described in (1) above, wherein the silica film thickness is from 0.1 to 25 nm.

(3) The silica-coated mixed crystal oxide particle as described in (1) or (2) above, wherein the photocatalytic activity determined by a tetralin auto-oxidation method is 60 Pa/min or less.

(4) The silica-coated mixed crystal oxide particle as described in any one of (1) to (3) above, wherein the silica film has a ratio I of the absorption peak intensity at from 1,150 to 1,250 cm$^{-1}$ to the absorption peak intensity at from 1,000 to 1,100 cm$^{-1}$ on the infrared absorption spectrum (I=$I_1/I_2$, wherein $I_1$ represents a maximum absorption peak intensity in the range of 1,150 to 1,250 cm$^{-1}$ and $I_2$ represents a maximum absorption peak intensity in the range of 1,000 to 1,100 cm$^{-1}$), of 0.2 or more and a refractive index of 1.435 or more.

(5) The silica-coated mixed crystal oxide particle as described in any one of (1) to (4) above, wherein a dye discoloration rate ($\Delta ABS_{490}$/hr) determined by a Sunset Yellow method is 0.1 or less.

(6) The silica-coated mixed crystal oxide particle as described in any one of (1) to (5) above, wherein the kinetic friction coefficient determined by a glass plate method is 0.55 or less.

(7) The silica-coated mixed crystal oxide particle as described in any one of (1) to (6) above, wherein in the vapor phase production method of producing a metal oxide by the high-temperature oxidization of a mixed gas containing a metal halide with an oxidizing gas, a mixed gas containing as the metal halide at least two compounds selected from the group consisting of chloride, bromide and iodide of titanium, silicon and aluminum, and an oxidizing gas each is preheated to 500° C. or more and reacted with each other to produce a metal oxide.

(8) The silica-coated mixed crystal oxide particle as described in (7) above, wherein the mixed gas containing a metal halide is a gas obtained by independently vaporizing each of at least two compounds selected from the group consisting of chloride, bromide and iodide of titanium, silicon and aluminum, and then mixing these compounds each in a gas state.

(9) The silica-coated mixed crystal oxide particle as described in any one of (1) to (8) above, wherein the mixed crystal oxide particle is a mixed crystal oxide particle containing a mixed crystal having a titanium-oxygen-silicon bond inside the primary particle.

(10) The silica-coated mixed crystal oxide particle as described in any one of (1) to (8) above, wherein the mixed crystal oxide particle is a mixed crystal oxide particle containing a mixed crystal having a titanium-oxygen-aluminum bond inside the primary particle.

(11) The silica-coated mixed crystal oxide particle as described in any one of (1) to (6) above, wherein the mixed crystal oxide particle is a composite oxide containing each crystal system structure of zinc oxide and silica, having diffraction peaks on the lattice faces (100), (002) and (101) which are diffraction peaks peculiar to crystalline zinc oxide in view of X-ray crystallography, and on the lattice face (101) which is a diffraction peak peculiar to crystalline silica, and mainly comprising zinc oxide.

(12) The silica-coated mixed crystal oxide particle as described in (11) above, wherein the mixed crystal oxide particle contains each crystal system structure of zinc oxide and silica in the primary particle.

(13) The silica-coated mixed crystal oxide particle as described in (11) or (12) above, wherein the mixed crystal oxide particle is a mixed crystal oxide particle containing a mixed crystal having a zinc-oxygen-silicon bond inside the primary particle.

(14) The silica-coated mixed crystal oxide particle as described in any one of (11) to (13) above, wherein the mixed crystal oxide particle is a composite oxide produced by a vapor phase reaction of oxidizing a gaseous zinc in the presence of oxygen and water vapor and in the vapor phase reaction, a Zn starting material gas containing a gaseous zinc in an inert gas, and an oxidizing gas containing oxygen and water vapor each is introduced into a reactor to allow the oxidation reaction of zinc to proceed inside the reactor and a silicon-containing composition is introduced into this reaction zone and oxidized.

(15) The silica-coated mixed crystal oxide particle as described in any one of (1) to (14) above, wherein the decrease percentage of the BET specific surface area after heating at 800° C. for 1 hour is 30% or less.

(16) The silica-coated mixed crystal oxide particle as described in any one of (1) to (15) above, wherein the surface of the silica film is hydrophobitized with a hydrophobicity-imparting agent.

(17) The silica-coated mixed crystal oxide particle as described in (16) above, wherein the hydrophobicity-imparting agent is one or more compound selected from the group consisting of silicone oils, alkoxysilanes, silane coupling agents and higher fatty acid salts.

(18) A production process of the silica-coated mixed crystal oxide particle described in any one of (1) to (17) above, comprising adding, in any order, a) a mixed crystal oxide particle having a BET specific surface area of 10 to 200 m$^2$/g and containing primary particles in a mixed crystal, b) a silicic acid containing neither an organic group nor a halogen or a precursor capable of producing the silicic acid, c) an alkali, d) an organic solvent and e) water such that the water/organic solvent ratio after the addition is from 0.1 to 10 and a silicon concentration is from 0.0001 to 5 mol/liter, thereby selectively forming a dense silica thin film on the surface of the mixed crystal oxide particle.

(19) A production process of the silica-coated mixed crystal oxide particle described in any one of (1) to (17) above, comprising adding d) a mixed crystal oxide particle having a BET specific surface area of 10 to 200 m$^2$/g and containing primary particles in a mixed crystal state to a mixed solution of a) an alkali, b) an organic solvent and c) water, and further adding a mixed solution of e) a silicic acid containing neither an organic group nor a halogen or a precursor capable of producing the silicic acid, f) an organic solvent and if desired, g) water such that the water/organic solvent ratio after the addition is from 0.1 to 10 and a silicon concentration is from 0.0001 to 5 mol/liter, thereby selectively forming a dense silica thin film on the surface of the mixed crystal oxide particle.

(20) The production process of the silica-coated mixed crystal oxide particle as described in (18) or (19) above, wherein the alkali is one or more member selected from the group consisting of ammonia, ammonium carbonate, ammonium hydrogencarbonate, ammonium formate and ammonium acetate.

(21) The production process of the silica-coated mixed crystal oxide particle as described in any one of (18) to (20) above, wherein the organic solvent is one or more member selected from the group consisting of methanol, ethanol, propanol, pentanol, tetrahydrofuran, 1,4-dioxane and acetone.

(22) A silica-coated mixed crystal oxide particle produced by the production process of the silica-coated mixed crystal oxide particle described in any one of (18) to (21) above.

(23) A cosmetic material comprising the silica-coated mixed crystal oxide particle described in any one of (1) to (17) and (22) above.

(24) The cosmetic material as described in (23) above, which comprises an antioxidant.

(25) The cosmetic material as described in (23) or (24) above, which comprises an organic ultraviolet absorber.

(26) An ultraviolet-protecting cosmetic preparation comprising the cosmetic material described in any one of (23) to (25) above.

(27) The ultraviolet-protecting cosmetic preparation as described in (26) above, which is a W/O or O/W milky lotion, a cream, a foundation or a gel.

BEST MODE FOR CARRYING OUT THE INVENTION

The present invention is described in detail below.

The silica-coated mixed crystal oxide particle (first aspect) which can be suitably used for the cosmetic material (third aspect) of the present invention, and a production process thereof (second aspect) are described below.

In the cosmetic material of the present invention, a silica-coated mixed crystal oxide particle where the surface of a mixed crystal oxide particle is covered with a silica film having a ratio I of the absorption peak intensity at 1,150 to 1,250 cm$^{-1}$ to the absorption peak intensity at 1,000 to 1,100 cm$^{-1}$ on the infrared absorption spectrum (I=I$_1$/I$_2$, wherein I$_1$ is a maximum absorption peak intensity in the range of 1,150 to 1,250 cm$^{-1}$ and I$_2$ is a maximum absorption peak intensity in the range of 1,000 to 1,100 cm$^{-1}$), of 0.2 or more and a refractive index of 1.435 or more, can be used.

The above-described silica-coated mixed crystal oxide particle which can be used in the cosmetic material of the present invention can be obtained by a method of adding, in any order, a silicic acid or a precursor capable of producing the silicic acid, an alkali, an organic solvent and if desired, water to a mixed crystal oxide particle such that the water/organic solvent ratio after the addition is, in terms of a volume ratio, from 0.1 to 10 and the silicon concentration is from 0.0001 to 5 mol/liter, thereby depositing silica on the surface of the mixed crystal oxide particle to form a silica film.

The silica-coated mixed crystal oxide particle is preferably obtained by a method of adding a mixed crystal oxide particle to a mixed solution of an alkali, an organic solvent and is desired, water, and further adding a mixed solution of a silicic acid or a precursor capable of producing the silicic acid, an organic solvent and if desired, water such that the water/organic solvent ratio after the addition is from 0.1 to 10 and the silicon concentration is from 0.0001 to 5 mol/liter, thereby depositing silica on the surface of the mixed crystal oxide particle to form a silica film.

The mixed crystal oxide particle as a starting material of the silica-coated mixed crystal oxide particle of the present invention is described below.

The mixed crystal oxide particle is an ultrafine particle oxide having a BET specific surface area of 10 to 200 m$^2$/g and containing primary particles in a mixed crystal state, which is obtained by a vapor phase production method of producing a metal oxide by the high-temperature oxidization of a metal halide with an oxidizing gas, where a mixed gas (hereinafter, sometimes referred to as "a mixed metal halide gas") containing as the metal halide at least two compounds selected from the group consisting of chloride, bromide and iodide of titanium, silicon and aluminum, and an oxidizing gas are each preheated to 500° C. or more and then reacted.

Furthermore, the mixed crystal oxide particle is a mixed crystal oxide particle having a BET specific surface area of 10 to 200 m$^2$/g and containing a mixed crystal where a titanium-oxygen-silicon bond or a titanium-oxygen-aluminum bond is present in the primary particle.

The mixed metal halide gas may be a gas obtained by individually vaporizing at least two compounds selected from the group consisting of chloride, bromide and iodide of titanium, silicon and aluminum, and then mixing these compounds each in a gas state.

In the embodiment of supplying the mixed metal halide gas to a reactor, a gas obtained by individually vaporizing metal halides and then mixing the metal halides each in a gas state is preferably used. For the oxidizing gas, oxygen, water vapor or a mixed gas containing these is used.

The chloride, the bromide and the iodide of titanium, silicon and aluminum for use in the present invention are not limited and any metal halide may be used insofar as it can generate the metal halide gas when preheated to at least 500° C. or more. In particular, TiCl$_4$, TiBr$_4$, SiCl$_4$ and AlCl$_3$ are preferred.

In the present invention, the above-described mixed metal halide gas and an oxidizing gas each must be preheated to at least 500° C. or more, preferably 650° C. or more, more preferably 800° C. or more, before the reaction. If the preheating temperature of the mixed metal halide gas and the oxidizing gas is less than 500° C., uniform cores are less generated and the reactivity is low, as a result, ultrafine particles are hardly obtained and residual halogen (chlorine, etc.) after desalting increases.

In the present invention, the mixed metal halide gas and the oxidizing gas each is preferably supplied to a reaction tube at a flow rate of 10 m/sec or more, preferably 30 m/sec or more. In the reaction tube, these gases are preferably reacted such that the time period in which the gases reside and react under high temperature condition exceeding 600° C. (hereinafter sometimes referred to as a "high-temperature residence time") is 1 second or less.

In view of the reaction, the flow rate at the time of introducing the mixed metal halide gas and the oxidizing gas to a reaction tube is preferably 10 m/sec or more, because by increasing the flow rate, the mixing of two gases can be accelerated. When the temperature at the introduction of gas to a reaction tube is 500° C. or more, the reaction is completed simultaneously with the mixing, therefore, the generation of uniform cores can be promoted and at the same time, the zone where particles grown under CVD (chemical vapor deposition) control are formed can be shortened.

The starting material gas is preferably introduced into a reaction tube, so that the gases introduced into the reactor can be thoroughly mixed. As long as the gases are thoroughly mixed, the fluid state of gas in the reaction tube is not particularly limited, however, for example, a fluid state of causing turbulence is preferred. Also, a spiral vortex may be present.

In the reaction tube, the flow rate of gas supplied inside the reaction tube is preferably higher for completely mixing the gases, in particular, preferably 5 m/sec or more as an average flow rate. As long as the flow rate of gas in the reactor is 5 m/sec or more, thorough mixing can be attained in the reaction tube.

The reaction in the reaction tube is an exothermic reaction and the reaction temperature is higher than the sintering temperature of the ultrafine particle titanium oxide produced. Although heat is radiated from the reaction apparatus, if the fine particles produced are not quenched after the reaction, the sintering proceeds and particles are grown. In the present invention, the high-temperature residence time exceeding 600° C. in the reaction tube is preferably 1 second or less and after that, the fine particles produced are preferably quenched.

As means for quenching the particles after the reaction, for example, introduction of a large amount of a cooling air or a gas such as nitrogen into the mixture after the reaction, or spraying of water thereon is employed.

The starting material mixed metal halide gas may be the mixed metal halide gas in 100 vol % or may be charged after diluting it preferably with an inert gas to a concentration of 10 to less than 100 vol %, more preferably from 20 to less than 100 vol %. When a gas having a mixed metal halide gas concentration (the total concentration of metal halide gases) of 10 vol % or more is used as the starting material, the generation of uniform cores is increased or the reactivity is elevated. For the above-described inert gas, a gas which does not react with the mixed metal halide and is not oxidized must be selected. Specific examples of preferred diluting gas include nitrogen and argon.

The mixed crystal oxide particle of the present invention has a BET specific surface area of 10 to 200 m$^2$/g and an average primary particle size of 0.008 to 0.1 μm, preferably from 0.015 to 0.1 μm.

The mixed crystal oxide particle of the present invention is a composite oxide mainly comprising zinc oxide, containing each crystal system structure of zinc oxide and silica, and having diffraction peaks on the lattice faces (100), (002) and (101) which are diffraction peaks peculiar to crystalline zinc oxide in view of X-ray crystallography, and on the lattice face (101) which is a diffraction peak peculiar to crystalline silica, where each crystal system structure of zinc oxide and silica is contained in the primary particle of composite oxide.

In the reaction of oxidizing a zinc vapor in an atmosphere where oxygen and water vapor are present, an inert gas containing zinc vapor (hereinafter sometimes referred to as a "Zn starting material gas") and a gas containing oxygen and water vapor (hereinafter sometimes referred to as an "oxidizing gas") each is introduced to a reactor to oxidize zinc. To this reaction site, a silicon-containing composition (hereinafter sometimes referred to as an "Si starting material") containing, for example, organosilane or silicon halide is introduced by spraying the composition in a liquid form or preferably introduced in a gas form, and the Si starting material is oxidized to obtain the composite oxide of the present invention. At this time, the Si starting material may contain an inert gas as a carrier gas.

The oxidizing gas may be a gas obtained by burning a combustible gas such as propane or hydrogen with an excess combustion-supporting gas such as oxygen or air. The nozzle for introducing an oxidizing gas, the nozzle for introducing the Zn starting material gas and the nozzle for introducing the Si starting material each may be composed of a plurality of nozzles.

The thus-obtained oxide is a mixed crystal oxide where crystalline silica is uniformly dispersed in the crystalline zinc oxide particle and which mainly comprises zinc oxide having excellent dispersibility. The term "mainly comprising" as used herein means a component occupying a largest portion among the constituent components. A component in 50 mass % or more is the main component.

This composite oxide has a strong diffraction peak on lattice faces (100), (002) and (101) peculiar to crystalline zinc oxide in view of X-ray crystallography and since silica is formed in the synthesis reaction site of zinc oxide where the temperature becomes very high, the particle can also have a strong diffraction peak on the lattice face (101) peculiar to crystalline silica in view of X-ray crystallography.

By local component analysis (EDX: energy dispersive X-ray spectroscopy), this composite oxide can be confirmed to be a composite oxide where silica microcrystals are uniformly dispersed in zinc oxide microcrystals. Conventional composite oxides are obtained by adding a second component after synthesizing a core substance and therefore, have a core-shell structure where the second component surrounds the periphery of the first component, or are a mere mixed powder where the first component particle and the second component particle are individually present.

The composite oxide of the present invention is a composite oxide where the crystalline second component (silica) is uniformly dispersed in the crystalline first component (zinc oxide) in all particles and diffraction peaks of both silica and zinc oxide are present in view of X-ray crystallography.

By local component analysis (EDX), Si component is confirmed to be uniformly present in the Zn component irrespective of the shape of these particles.

An inert gas can also be supplied to a zinc vaporizer simultaneously with the starting material metal zinc. Examples of the inert gas include nitrogen, helium and argon.

The Zn starting material gas is then introduced into a reactor from the zinc vaporizer through a Zn starting material gas heater. The temperature in introducing the Zn starting material gas into the reactor is from 900 to 1,800° C., preferably from 900 to 1,500° C., more preferably from 950 to 1,300° C. The speed in introducing the Zn starting material gas into a reactor is from 10 to 250 m/sec, preferably from 50 to 150 m/sec.

The temperature in introducing the oxidizing gas into the reactor is from 900 to 1,800° C., preferably from 900 to 1,500° C., more preferably from 950 to 1,300° C. The oxygen concentration of the oxidizing gas is from 5 to 100 vol %, preferably from 50 to 100 vol %.

The silicon-containing composition is vaporized together with an inert gas as a carrier gas and introduced into the reactor. The silicon-containing composition is a composition containing organosilane or silicon halide.

The temperature in introducing the Si starting material into the reactor is from 50 to 1,200° C., preferably from the boiling point of the silicon-containing composition to the decomposition temperature thereof. For example, in the case of using tetraethoxysilane, the introduction temperature is preferably from 170 to 400° C. where tetraethoxysilane is not decomposed and is in a gas form.

The amount of the Si starting material supplied is set such that the Si content of the composite oxide obtained is, in terms of silica, preferably from 5 to less than 50 mass %, more preferably from 5 to less than 35 mass %.

The introduction flow rate of the Si starting material is very important in determining the silica distribution within a composite oxide particle. In the case of using a coaxial parallel flow nozzle, the introduction flow rate of the gaseous Si starting material is adjusted to from 30 to 300%, preferably from 80 to 150%, of the flow rate of the Zn starting material gas, whereby silica can be uniformly dispersed in the composite oxide particle of the present invention.

Also, by adjusting this introduction flow rate to exceed 150% of the flow rate of the Zn starting material gas, silica can be localized in the vicinity of the surface in a larger amount than in the central part of particle. In the case where the nozzle used is not a coaxial nozzle, the same effect can be obtained by turning the introducing direction toward the downstream side and the reaction zone of the Si starting material is arranged to come in the downstream side than the reaction zone of zinc.

With respect to the particle shape, the ratio of tetrapod-like and needle-like particles can be increased by reducing the amount of the silicon-containing composition introduced. The ratio of tetrapod-like and needle-like particles affects the dispersibility of a composite oxide in a medium and is preferably from 5 to 95% by number, more preferably from 40 to 90% by number.

As long as the Zn starting material gas, the oxidizing gas and the Si starting material each satisfies the above-described conditions, the oxidation reaction rapidly proceeds in any introduction form such as coaxial parallel flow, cross flow or oblique flow.

The oxidation reaction thereof proceeds in a reactor at a high temperature. In order to more completely inhibit the growth of particle, the high-temperature residence time may be controlled, for example, by a method of quenching particles at a specific position.

The mixed crystal oxide particle of the present invention is characterized in that in the evaluation of the decrease percentage of the BET specific surface area after heating, which is an index of the sintering resistance, the decrease percentage of the BET specific surface area after heating at 800° C. for one hour is 30% or less.

The silicic acid for use in the silica film-forming composition is an orthosilicic acid or a polymer thereof such as metasilicic acid, mesosilicic acid, mesotrisilicic acid or mesotetrasilicic acid, described, for example, in *Encyclopaedia Chimica,* "Silicic Acid", 7th imp., Kyoritsu Shuppan (Mar. 15, 1969).

The composition containing a silicic acid can be obtained by adding water, an alkali and an organic solvent to a precursor capable of producing the above-described silicic acid, for example, tetraalkoxysilane ($Si(OR)_4$, wherein R is a hydrocarbon group; specifically, tetramethoxysilane, tetraethoxysilane, tetra-n-propoxysilane, tetraisopropoxysilane, tetra-n-butoxysilane, etc.), and stirring the mixture to allow a hydrolysis reaction to proceed. This method is preferred because handling or operation is easy and practical. Among those materials, tetraethoxysilane is preferred.

The composition containing a silicic acid can also be obtained by a method of hydrolyzing silane tetrahalide by adding thereto water, an alkali and an organic solvent, a method of adding an alkali and an organic solvent to water glass, or a method of treating water glass with a cationic exchange resin and adding thereto an alkali and an organic solvent.

The tetraalkoxysilane, silane tetrahalide, water glass and the like used as the precursor capable of producing silicic acid are not particularly limited and those widely and commonly used in industry or as a reagent may be used, however, a material having a higher purity is preferred. The composition for forming a silica film of the present invention may contain an unreacted material of the above-described starting material of the silicic acid.

The amount of the silicic acid is not particularly limited, however, in terms of the silicon concentration, it is preferably from 0.0001 to 5 mol/liter. If the silicon concentration is less than 0.0001 mol/liter, the silica film is formed at a very low rate and this is not practical, whereas if it exceeds 5 mol/liter, the coating is not formed on the surface of the metal oxide but silica particles may be produced in the composition.

The silicon concentration may be calculated from the amount added of the starting material of the silicic acid, for example, tetraalkoxysilane, but can also be measured by the atomic absorption spectrometry of the composition. The measurement is preferably performed using a spectrum of silicon at a wavelength of 251.6 nm as the analysis line and an acetylene/nitrous oxide flame.

The water for use in the silica film-forming composition is not particularly limited but water from which particles are removed by filtration or the like is preferred. If particles are contained in the water, the particles are disadvantageously mixed into the product as an impurity.

The water is preferably used in an amount of giving a water/organic solvent ratio by volume of 0.1 to 10. If the water/organic solvent ratio departs from this range, the film formation may fail or the film formation rate may decrease seriously. The water/organic solvent ratio by volume is more preferably from 0.1 to 0.5. As long as the water/organic solvent ratio is in the range of 0.1 to 0.5, the kind of alkali used is not limited. In the range outside this, namely, in the case where the water/organic solvent ratio is 0.5 or more, the coating is preferably formed using an alkali metal-free alkali such as ammonia, ammonium hydrogencarbonate and ammonium carbonate.

The alkali for use in the silica film-forming composition is not particularly limited, however, examples thereof include inorganic alkalis such as ammonia, sodium hydroxide and potassium hydroxide; inorganic alkali salts such as ammonium carbonate, ammonium hydrogencarbonate, sodium carbonate and sodium hydrogencarbonate; organic alkalis such as monomethylamine, dimethylamine, trimethylamine, monoethylamine, diethylamine, triethylamine, pyridine, aniline, choline, tetramethylammonium hydroxide and guanidine; and alkali salts of organic acid, such as ammonium formate, ammonium acetate, monomethylamine formate, dimethylamine acetate, pyridine lactate, guanidinoacetic acid and aniline acetate.

These alkalis may be used individually or in combination of two or more thereof. Among these, ammonia, ammonium carbonate, ammonium hydrogencarbonate, ammonium formate, ammonium acetate, sodium carbonate and sodium hydrogencarbonate are preferred.

The purity of the alkali for use in the present composition is not particularly limited and an alkali widely and commonly used in industry or as a reagent may be used, but an alkali having a higher purity is preferred.

The effective means for increasing the film-forming rate is to elevate the temperature at the time of film formation. In this case, an alkali and an organic solvent difficult to volatilize or decompose at the film formation temperature are preferably used.

Even when the alkali is added in a slight amount, for example, in the case of sodium carbonate, on the order of 0.002 mol/liter, the film formation may be attained but the alkali may also be added in a large amount on the order of 1 mol/liter. However, if a solid alkali is added in excess of solubility, the alkali is mixed into the silica-coated mixed crystal oxide particle as an impurity and this is not preferred.

By using an alkali not containing an alkali metal as a main component, a silica-coated mixed crystal oxide particle reduced in the alkali metal content can be produced. Among such alkalis, ammonia, ammonium carbonate and ammonium hydrogencarbonate are preferred in view of high film formation rate and easiness in the removal of residual matter.

The organic solvent used for the film-forming composition is preferably an organic solvent which can provide the composition as a uniform solution. Examples thereof include alcohols such as methanol, ethanol, propanol and pentanol; ether-acetals such as tetrahydrofuran and 1,4-dioxane; aldehydes such as acetaldehyde; ketones such as acetone, diacetone alcohol and methyl ethyl ketone; and polyhydric alcohol derivatives such as ethylene glycol, propylene glycol and diethylene glycol. Among these, alcohols are preferred and ethanol is more preferred. These organic solvents may be used individually or in combination of two or more thereof.

The purity of the organic solvent for use in the present composition is not particularly limited and an organic solvent widely and commonly used in industry or as a reagent may be used, but an organic solvent having a higher purity is preferred.

For the preparation of the silica film-forming composition, a general solution preparation method may be used. For example, a method of, adding an alkali, water and an organic solvent to a predetermined amount of mixed crystal oxide particles, stirring the solution to thoroughly disperse the mixed crystal oxide particles, adding tetraethoxysilane, and stirring the mixture, may be used. In this mixing, whichever added earlier or even if the mixing is repeated two or more times, a coating can be formed. In mixing water and tetraethoxysilane, both are preferably diluted with an organic solvent in view of the control of reaction.

The thus-prepared silica film-forming composition is a stable composition and causes substantially no deposition or precipitation before the composition is brought into contact with mixed crystal oxide particles. When the mixed crystal oxide particle is contacted with the composition, silica film is selectively formed on the surface of the mixed crystal oxide particle.

The term "selectively" as used herein means that the film formation accompanying the precipitation of silica proceeds only on the surface of the mixed crystal oxide particle but production of silica particles accompanying the generation of uniform cores in the solution is not brought about and therefore, the silica film thickness and silica content of the silica-coated mixed crystal oxide particle can be stoichiometrically controlled.

Fundamentally, the mixed crystal oxide particle is added to the silica film-forming composition and kept at a predetermined temperature, whereby silica can be selectively deposited on the surface of the mixed crystal oxide particle to form silica film. Also, for example, a method of previously preparing the film-forming composition and charging mixed crystal oxide particles into the composition to form a silica film, a method of previously suspending mixed crystal oxide particle in a solvent, adding other starting material components to prepare a film-forming composition and forming a silica film may be used. In other words, the order of charging starting materials of the film-forming composition and mixed crystal oxide particles is not particularly limited and whichever charged earlier, a silica film can be formed.

Among these methods, a method of preparing a suspension from mixed crystal oxide particle, water, an organic solvent and an alkali and charging thereinto tetraalkoxysilane diluted with an organic solvent, with the passage of time is preferred, because a silica film having good denseness can be formed and a continuous process useful in industry can be established.

Furthermore, a method of adding mixed crystal oxide particles to a mixed solution of an organic solvent, water and an alkali and charging thereinto an organic solvent and depending on the case, tetraalkoxysilane diluted with water, with the passage of time is preferred, because a silica film having good denseness can be formed and a continuous process useful in industry can be established.

The silica film grows by the deposition on the surface of a mixed crystal oxide particle and therefore, as the film formation time is longer, the coating can have a larger thickness. Of course, when the majority of silicic acid or a precursor thereof in the film-forming composition is consumed by the formation of coating, the film formation rate decreases, however, by sequentially adding silicic acid or a precursor thereof in an amount corresponding to the consumed portion, the silica film can be continuously formed at a practical film formation rate.

In particular, after holding mixed crystal oxide particles in the film-forming composition having added thereto a silicic acid corresponding to the desired thickness of silica film for a predetermined time to form a silica film and then taking out the silica-coated mixed crystal oxide particles from the system, an organic solvent, a volatile alkali and the like can be recovered in the separation and purification process and used in the next film formation on a mixed crystal oxide particle and therefore, a process having high profitability and high productivity can be established.

The temperature at the film formation is not particularly limited but is preferably from 10 to 100° C., more preferably from 20 to 50° C. As the temperature is higher, the film formation rate more increases, however, if the temperature is excessively high, the solution composition cannot be maintained constant due to volatilization of components in the composition, whereas if the temperature is too low, the film formation proceeds at a low rate and this is not practical.

The pH at the film formation may be sufficient if it is in the alkali region. However, a pH where mixed crystal oxide particles are not gelled is preferred. In the case of coating silica on a mixed crystal oxide particle having a solubility which increases depending on the pH, the pH of the film-forming composition is preferably controlled.

For example, in the production of a silica-coated article of ultrafine mixed crystal oxide particle mainly comprising zinc oxide, the pH at the formation is preferably controlled to 11 or less by reducing the amount of alkali added. If the pH exceeds 11, the yield of the silica-coated product may decrease. With the reduction in the amount of alkali added, the film formation rate decreases and therefore, it is preferred to maintain the practical film formation rate by elevating the film formation temperature or increasing the silicon concentration.

After the film formation, an unreacted starting material, an alkali and an organic solvent are removed and if desired, the residue is concentrated, whereby silica-coated mixed crystal oxide particle is obtained. The removal may be performed by a general separation method such as evaporation, distillation and membrane separation.

The medium for the silica-coated sol of the present invention is not particularly limited, however, is usually selected from dermatologically harmless mediums. For example, water, natural oil or silicone oil is used. The change from aqueous medium to other medium can be performed by a general method such as solvent displacement or membrane separation.

When the silica-coated mixed crystal oxide particle sol is subjected to a solid-liquid separation and then, dried, a silica-coated mixed crystal oxide particle can be obtained. The solid-liquid separation may be performed by a general separation method such as filtration, centrifugal sedimentation and centrifugal separation. In the drying, a general drying method may be used, such as natural drying, hot air drying, vacuum drying and spray drying. In the case where aggregation of particles occurs by the drying, the aggregate may be ground. In the silica-coated mixed crystal oxide particle of the present invention, the covering power of silica film on the surface of mixed crystal oxide particle as a substrate is strong and therefore, it does not occur that the silica film is broken by the grinding to decrease the effect of preventing the photocatalytic activity or worsen the feeling on use. The grinding method is not particularly limited and a jet mill, a high-speed rotary mill or the like may be used.

In the silica film obtained by the above-described production method, the ratio I of the absorption peak intensity at 1,150 to 1,250 $cm^{-1}$ to the absorption peak intensity at 1,000 to 1,100 $cm^{-1}$ on the infrared absorption spectrum ($I=I_1/I_2$, wherein $I_1$ represents an maximum peak intensity in the absorption range of 1,150 to 1,250 $cm^{-1}$ and $I_2$ represents a maximum absorption peak intensity in the range of 1,000 to 1,100 $cm^{-1}$) is 0.2 or more and the refractive index is 1.435 or more.

In other words, this silica coating can be a dense and practical film which has been heretofore not obtained unless burnt, while maintaining the original surface physical properties (wet feeling and lubricity) of the silica film. Furthermore, this silica film has good conformability to a complicated shape of the mixed crystal oxide particle as the substrate and even if the thickness is as small as about 0.1 nm, the coating exhibits good covering power and high capability of concealing the photocatalytic activity. In addition, since the silica coating can be extremely reduced in the alkali metal content, the silica film is not dissolved even in an atmosphere of high temperature and high humidity and the silica-coated mixed crystal oxide particle obtained can be prevented from changing in the physical properties.

For the cosmetic material of the present invention, a surface-hydrophobitized silica-coated mixed crystal oxide particle obtained by further surface-treating the above-described silica-coated mixed crystal oxide particle with a hydrophobicity-imparting agent can also be used.

The surface-treatment of the silica-coated mixed crystal oxide particle with a hydrophobicity-imparting agent can be performed using a known method. In the present invention, a wet process is preferably used because the dispersibility and small primary particle size of the silica-coated mixed crystal oxide particle are not impaired. For example, the wet process may be performed using a method of dispersing the silica-coated mixed crystal oxide particles in water, an organic solvent or a mixed solvent, adding thereto a hydrophobicity-imparting agent or a solution thereof, a reaction catalyst and the like, further stirring the solution and then, performing the surface-treatment.

The silica-coated mixed crystal oxide particle can be directly hydrophobitized using a dry process or a spray process. The dry process may be performed using a method where a hydrophobicity-imparting agent or a solution of a hydrophobicity-imparting agent dissolved in an organic solvent is added by spraying or the like to the above-described silica-coated mixed crystal oxide particles under stirring in a mixer such as V-type mixer or Henschel mixer, the mixing is further continued to thereby allow the hydrophobicity-imparting agent to uniformly adhere to the surface of the power particle, and the powder particles are dried and if desired, heated for achieving firm adhesion. The spray process may be performed using a method of spraying a hydrophobicity-imparting agent or a solution thereof on the silica-coated mixed crystal oxide particle set to a high temperature, thereby covering the particle surface with the hydrophobicity-imparting agent.

The hydrophobicity-imparting agent for use in the present invention is not particularly limited, however, examples thereof include higher fatty acids such as wax, higher fatty acid triglyceride, higher fatty acid, higher fatty acid polyvalent metal salt and polyvalent metal salt of higher aliphatic sulfated product; higher alcohols and derivatives thereof; organic fluorine compounds such as perfluorinated or partially fluorinated higher fatty acid or higher alcohol; and organic silicon compounds such as silicone oils, organic alkoxysilanes, organic chlorosilanes and silazanes. Among these, a higher fatty acid polyvalent metal salts, a silicone oil, a silane coupling agent and alkoxysilanes are preferred, and in view of practical effect, alkoxysilanes and a silane coupling agent are more preferred.

The silicone oils for use in the present invention are not particularly limited, however, examples thereof include dimethylpolysiloxane, methylhydrogenpolysiloxane, methylphenylpolysiloxane and cyclic polydimethylsiloxane. A denatured silicone oil such as alkyl-denatured, polyether-denatured, amino-denatured, mercapto-denatured, epoxy-denatured and fluorine-denatured silicone oils may also be used.

The chlorosilanes for use in the present invention are not particularly limited, however, examples thereof include trimethylchlorosilane, dimethyldichlorosilane, methyltrichlorosilane, methyldichlorosilane, dimethylvinyl-chlorosilane, methylvinyldichlorosilane, triphenylchloro-silane, methyldiphenylchlorosilane, diphenyldichlorosilane, methylphenyldichlorosilane and phenyltrichlorosilane.

The silazanes for use in the present invention are not particularly limited, however, examples thereof include hexamethyldisilazane, N,N'-bis(trimethylsilyl)urea, N-trimethylsilylacetamide, dimethyltrimethylsilylamine, diethyltrimethylsilylamine and trimethylsilylimidazole.

The organic alkoxysilanes for use in the present invention are not particularly limited, however, examples thereof include silane coupling agents such as vinyl-trichlorosilane, vinyltris(β-methoxyethoxy)silane, vinyl-trimethoxysilane, vinyltriethoxysilane, γ-(methacryloyl-oxypropyl)trimethoxysilane, β-(3,4-epoxycyclohexyl)ethyl-trimethoxysilane, γ-glycidyloxypropyltrimethoxysilane, γ-glycidoxypropylmethyldiethoxysilane, N-β-(aminoethyl)-γ-aminopropyltrimethoxysilane, N-β-(aminoethyl)-γ-amino-propylmethyldiethoxysilane, γ-aminopropyltriethoxysilane, N-phenyl-γ-aminopropyltrimethoxysilane, γ-mercaptopropyltrimethoxysilane and γ-chloropropyltrimethoxysilane, methyltrimethoxysilane, dimethyldimethoxysilane, trimethyl-methoxysilane, methyltriethoxysilane, dimethyldiethoxysilane, trimethylethoxysilane, methyldimethoxysilane, methyldiethoxysilane, dimethylethoxysilane, dimethylvinyl-methoxysilane, dimethylvinylethoxysilane, phenyltrimethoxy-silane, phenyltriethoxysilane, diphenyldimethoxysilane and diphenyldiethoxysilane. An alkoxysilane having a perfluorinated or partially fluorinated alkyl group can also be used.

In particular, an alkylalkoxysilane represented by the following formula (1) is preferably used:

$$R^1(R^2_n)SiX_{3-n} \quad (1)$$

(wherein $R^1$ represents an alkyl group having from 1 to 4 carbon atoms or a phenyl group, $R^2$ represents a hydrogen group, an alkyl group having from 1 to 4 carbon atoms or a phenyl group, X represents an alkoxy group having from 1 to 4 carbon atoms, and n represents an integer of 0 to 2).

In the case of performing the surface treatment using an alkylalkoxysilane as a hydrophobicity-imparting agent, a liquid phase process is particularly preferred.

More specifically, after coating silica on the mixed crystal oxide particle according to the above-described method, without separating the silica-coated mixed crystal oxide particles, a hydrophobicity-imparting agent and if desired, water, an organic solvent and an alkali are added to form a composition where the water/organic solvent ratio is 0.1 to 10 and the concentration of silicon originated in the alkylalkoxysilane is from 0.0001 to 5 mol/liter, and the reaction product of alkylalkoxysilane is selectively deposited on the surface of the silica-coated mixed crystal oxide particle, whereby the surface treatment can be performed.

This method is industrially useful because the dispersibility and small primary particle size of the silica-coated mixed crystal oxide particle are not impaired due to absence of drying step and the intermediate solid separation step can be omitted.

In the production process of a silica-coated mixed crystal oxide particle surface-hydrophobitized with an alkylalkoxysilane, the water/organic solvent ratio by volume in the hydrophobitizing composition is from 0.1 to 10 and the concentration of silicon originated in the alkylalkoxysilane is from 0.0001 to 5 mol/liter. With respect to the silicon concentration, water, water/organic solvent ratio, alkali, organic solvent, temperature, pH and separation/purification step for the hydrophobitizing composition, the description for the silica film-forming composition can be applied as it is. The hydrophobitizing composition can be obtained by adding alkylalkoxysilanes in place of a precursor capable of producing a silicic acid to the silica film-forming composition after the completion of formation of silica coating, however, the composition and the conditions are not necessarily the same. For example, in the case where the alkylalkoxysilane is different in the reaction rate from the precursor capable of producing silicic acid, an alkali, water or a solvent may be added, if desired, and reaction conditions of giving a practical reaction rate, such as water/organic solvent ratio, silicon concentration, pH and temperature, can be selected within the above-described limits.

The coverage of the hydrophobicity-imparting agent may be sufficient if it is the minimum coverage or more capable of completely covering the surface of starting material silica-coated mixed crystal oxide particle. This coverage can be calculated by the following formula (2):

$$\text{Coverage (g) of hydrophobicity-imparting agent} = \frac{\text{Mass (g) of silica-coated mixed crystal oxide particle} \times \text{specific surface area (m}^2\text{/g)}}{\text{Minimum coated area with hydrophobicity-imparting agent (m}^2\text{/g)}} \quad (2)$$

If the amount of the hydrophobicity-imparting agent added is excessively large, the amount of the hydrophobicity-imparting agent deposited other than the surface of the silica-coated mixed crystal oxide particle increases and this is not profitable.

The amount of the hydrophobicity-imparting agent added varies depending on the molecular weight of the hydrophobicity-imparting agent and the specific surface area of the particulate silica-coated mixed crystal oxide and therefore, cannot be indiscriminately specified, however, usually, the amount added is preferably 30 mass % or less, more preferably 20 mass % or less, based on the silica-coated mixed crystal oxide particle.

The second aspect of the present invention is described below. The silica film thickness of the silica-coated mixed crystal oxide particle which can be used in the cosmetic material of the present invention is preferably 0.1 to 25 nm. If the silica film thickness is less than 0.1 nm, the cosmetic material obtained may fail in giving good feeling on use and having a sufficiently high effect of preventing the photocatalytic activity, whereas if it exceeds 25 nm, a cosmetic material having a sufficiently high ultraviolet-shielding ability may not be obtained and also, this is not profitable.

The photocatalytic activity measured by a tetralin auto-oxidation method of the silica-coated mixed crystal oxide particle of the present invention is 60 Pa/min or less, preferably 50 Pa/min or less, more preferably 45 Pa/min or less. If the photocatalytic activity exceeds 60 Pa/min, a sufficiently high effect of preventing the photocatalytic activity cannot be obtained and a cosmetic material having good storage stability may not be obtained.

The dye discoloration rate measured by a Sunset Yellow method of the silica-coated mixed crystal oxide particle of the present invention is 0.1 or less, preferably 0.06 or less, more preferably 0.02 or less. If the dye discoloration rate exceeds 0.1, the effect of preventing the photocatalytic activity is not sufficiently high and a cosmetic composition having high storage stability may not be obtained.

The primary particle size of the silica-coated mixed crystal oxide particle of the present invention is preferably from 1 to 100 nm. If the primary particle size is not in this range, a cosmetic material having all of good use feeling, transparency and high ultraviolet-shielding effect may not be obtained. The primary particle and the second particle as used in the present invention indicate particles defined in Kiichiro Kubo et al. (compilers), *Funtai (Powder)*, pp. 56-66 (1979).

The powder kinetic friction coefficient determined by a glass plate method of the silica-coated mixed crystal oxide particle of the present invention is 0.55 or less, preferably 0.5 or less, more preferably 0.45 or less. If it exceeds 0.55, a cosmetic material having good use feeling may not be obtained.

The silica-coated mixed crystal oxide particle of the present invention has a small primary particle size, a low cohesiveness and good dispersibility and therefore, has high ultraviolet-shielding ability and high visible light transmittance. Furthermore, since the silica-coated mixed crystal oxide particle is covered with a dense and practical silica film, the effect of preventing the photocatalytic activity is high, other ingredients blended in cosmetic material are less denatured and the touch feeling and lubricity are good.

Accordingly, by blending the silica-coated mixed crystal oxide particle, an ultraviolet-shielding cosmetic material ensuring good storage stability, safety, high transparency and good feeling on use can be obtained. The surface-hydrophobitized silica-coated mixed crystal oxide particle is preferably used for oily cosmetic materials, W/O emulsion-type cosmetic materials and water-repellent cosmetic materials reduced in falling by sweat or water.

The third aspect is described below. The cosmetic material of the present invention contains the above-described silica-coated mixed crystal oxide particles and can be produced using normal starting materials which can be blended in cosmetic materials, by an ordinary production process.

The cosmetic material of the present invention is not particularly limited insofar as it contains powder and oil. The cosmetic material of the present invention includes those obtained by dispersing the powder in a solvent or a solution. Examples thereof include face powder, foundation, cosmetic powder, cheek color product, eyeshadow, lipstick, eyeliner, mascara, eyebrow product, cream, essence, lotion, skin lotion, milky lotion and mousse. Among these, in the case of a surface-hydrophobitized silica-coated mixed crystal oxide particle, oily cosmetic materials, W/O emulsion-type cosmetic materials and water-repellent cosmetic materials reduced in falling by sweat or water are preferred.

The cosmetic material of the present invention is composed of a powder portion and an oil portion. The ingredient constituting the powder portion includes, in addition to the silica-coated mixed crystal oxide particle, an extender pigment (e.g., mica, talc, kaolin, calcium carbonate, magnesium carbonate, silicic acid anhydride, aluminum oxide, barium sulfate), a white pigment (e.g., titanium dioxide, zinc oxide) and a color pigment (e.g., red oxide of iron, yellow oxide of iron, black oxide of iron, chromium oxide, ultramarine, iron blue, carbon black). These ingredients may be appropriately blended. In order to further improve the feeling on use, a spherical powder (e.g., nylon powder, polymethyl methacrylate powder) may also be used.

The ingredient constituting the oil portion blended in the cosmetic material of the present invention includes liquid petrolatum, squalane, castor oil, glyceryl diisostearate, glyceryl triisostearate, glyceryl tri-2-ethylhexanoate, isopropyl myristate, glyceryl triisostearate, dimethylpolysiloxane, methylphenyl polysiloxane, petrolatum, diisostearyl maleate, purified lanolin and the like. The amount of the oil portion blended is preferably from 1 to 35 mass %, more preferably from 3 to 30 mass %, most preferably from 10 to 25 mass %, based on the cosmetic material of the present invention.

In the oil portion, an organic ultraviolet absorber may also be blended. The organic ultraviolet absorber means an organic compound having a function of absorbing an ultraviolet ray, consuming the energy for the generation of heat, oscillation, fluorescence, radical or the like, and thereby protecting skin.

The ultraviolet absorber which can be used in the cosmetic material of the present invention is not particularly limited but examples thereof include ultraviolet absorbers of benzophenone type, salicylic acid type, PABA type, cinnamic acid type, dibenzoylmethane type and urocanic acid type. The blended amount thereof is from 0.1 to 10 mass %, however, an appropriate amount is preferably determined according to the ultraviolet ray-absorbing power of the absorber. Even when the silica-coated mixed crystal oxide particle for use in the present invention is used in combination with the organic ultraviolet absorber, the absorber can be prevented from decomposing, so that the obtained cosmetic material can have high ultraviolet-shielding ability.

The cosmetic material of the present invention may further contain an existing emulsifier in a general concentration. Examples of the emulsifier include those described in *Japanese Standards of Cosmetic Ingredients (JSCI), 2nd Edition, Annotation,* compiled by Nippon Koteisho Kyokai, issued by Yakuji Nippo, Ltd. (1984), *Specifications of Ingredient Other Than Those Listed in JSCI,* supervised by Examination Division, Pharmaceutical Affairs Bureau, Ministry of Health and Welfare, issued by Yakuji Nippo, Ltd. (1993), *Specifications of Ingredient Other Than Those Listed in JSCI, Supplement,* supervised by Examination Division, Pharmaceutical Affairs Bureau, Ministry of Health and Welfare, issued by Yakuji Nippo, Ltd. (1993), *The Comprehensive Licensing Standards of Cosmetics by Category,* supervised by Examination Division, Pharmaceutical Affairs Bureau, Ministry of Health and Welfare, issued by Yakuji Nippo, Ltd. (1993), and *Kesho-hin Genryo Jiten (Handbook of Cosmetic Ingredients),* Nikko Chemicals (1991). All emulsifies described in these publications can be used. In addition, tocopheryl phosphates may also be used as the emulsifier.

In the cosmetic material of the present invention, an existing antiinflammatory or antiphlogistic ingredient may be used in combination or may be mixed so as to protect against inflammation by ultraviolet rays, as long as there is no problem in the safety. Examples of the antiphlogistic ingredient which can be added to the cosmetic material of the present invention include aniline derivative-type antiphlogistic, salicylic acid derivative-type antiphlogistic, pyrazolone derivative-type antiphlogistic, indomethacin-type antiphlogistic, mefenamic acid-type antiphlogistic, antihistamin agent, antiallergic agent and antiinflammatory enzymatic agent.

When an antioxidant as a substance having an oxidation-inhibiting activity is used in combination in the cosmetic material containing silica-coated mixed crystal oxide particles of the present invention, the amount of free radicals generated by ultraviolet rays can be reduced and thereby a cosmetic material having an extremely low phototoxicity can be obtained.

The antioxidant which can be used in the cosmetic material of the present invention is not particularly limited but examples thereof include vitamin A, β-carotene, astaxanthin, vitamin B, vitamin C, magnesium L-ascorbic acid-2-phosphate, sodium L-ascorbic acid-2-phosphate, magnesium sodium L-ascorbic acid-2-phosphate, L-ascorbic acid-2-glucoside-6-palmitate, L-ascorbic acid-2-phosphoric acid-6-palmitate, L-ascorbic acid-2-phosphoric acid-5,6-benzylidene, natural vitamin E, dl-α-tocopherol, dl-α-tocopheryl acetate, sodium dl-α-tocopheryl phosphate, ubiquinone, derivatives of these vitamins, cysteine, glutathione, glutathione peroxidase, SOD, catalase, citric acid, phosphoric acid, polyphenol, catechine, tea extract, kojic acid, nucleic acid, hydroquinone and arbutin. One or more antioxidants selected from these may be blended.

Other than the above-described ingredients, the cosmetic material according to the present invention may contain ingredients commonly blended in cosmetic materials, such as fats and oils, waxes, hydrocarbons, fatty acids, alcohols, polyhydric alcohols, saccharides, esters, metal soap, water-soluble polymer compound, surfactant, antioxidant, microbicide·antiseptic, vitamin, hormone and coloring material.

The amount of the silica-coated mixed crystal oxide particle blended in the cosmetic material of the present invention is preferably from 1 to 50 mass %, more preferably from 3 to 40 mass %, most preferably from 5 to 30 mass %, based on the cosmetic material.

When in the silica-coated mixed crystal oxide particle used for the cosmetic material of the present invention, an ultra-fine particulate silica-coated mixed crystal oxide having a large specific surface area is dispersed in a good state, the cosmetic material can have particularly high ultraviolet-shielding ability and the amount of the silica-coated mixed crystal oxide particle added can be reduced. The metal oxide sol and/or surface-hydrophobitized silica-coated metal oxide sol contained in the cosmetic material of the present invention has a small primary particle size and is covered with a dense and practical silica film and therefore, even when the cosmetic material is blended in a high concentration, excellent feeling on use is ensured without causing any creaky feeling or poor extension.

Furthermore, in the silica-coated metal oxide sol and/or surface hydrophobitized silica-coated metal oxide sol used for the cosmetic material of the present invention, metal oxide particles having a small particle size are dispersed in a good state and therefore, the cosmetic material can have excellent visible light transmittance and highly transparent make-up finish.

In addition, the surface of the metal oxide fine particles is covered with a dense and practical silica film, so that the photocatalytic activity ascribable to the metal oxide can be satisfactorily prevented, other ingredients blended in the cosmetic material can be protected from denaturing and excellent storage stability can be obtained.

The cosmetic material of the present invention may contain an organic ultraviolet absorber, so that higher ultraviolet-shielding effect can be achieved. Furthermore, by containing an antioxidant, generation of active oxygen and the like can be greatly reduced and therefore, the safety to human body can be enhanced.

In the present invention, the thickness and the refractive index of the silica film can be measured by using a silica film formed on a silicon wafer immersed in a system undergoing the synthesis of silica-coated mixed crystal oxide particle. On this silicon wafer, the same silica film as on the mixed crystal oxide particle of the silica-coated mixed crystal oxide particle is formed. The refractive index of silica film can be determined by an ellipsometer (LASSER ELLIPSOMETER ESM-1A, manufactured by ULVAC). The thickness can be determined using a step gauge. The transmission infrared absorption spectrum of silica film of the silica-coated mixed crystal oxide particle can be determined by FT-IR-8000 manufactured by JASCO Corp.

The primary particle size of the silica-coated mixed crystal oxide particle and the thickness of silica film thereof can be determined from an image by a transmission electron microscope. The total alkali metal content is determined using the flame analysis by dissolving a silica-coated mixed crystal oxide particle in a fluorosulfuric acid.

The photocatalytic activity, namely, the initial oxygen consumption rate, of the silica-coated mixed crystal oxide particle can be measured by a tetralin auto-oxidation method (see, Manabu Kiyono, *Sanka Titan-Bussei to Oyo Gijutsu (Titanium Oxide—Physical Properties and Applied Technique),* pp. 196-197, Gihodo (1991)). The measurement conditions are such that the temperature is 40° C., tetralin is 20 ml and the mixed crystal oxide particle having a solid content concentration of 10% is 0.02 g.

The decomposition rate, powder kinetic friction coefficient and dye discoloration rate of the organic ultraviolet absorber in the silica-coated mixed crystal oxide particle of the present invention are determined by a Parsol method, a glass plate method and a Sunset Yellow method, respectively, which are described in the present specification.

EXAMPLES

The present invention is described in greater detail below by referring to the Examples. However, the present invention is not limited to these Examples.

Example 1

Production of Mixed Crystal Oxide Particle 1

To a zinc vaporizer, 3.8 kg/hr of metal zinc and 25 Nm$^3$/hr (N indicates the standard state, hereinafter the same) of nitrogen gas heated at 900° C. were supplied to obtain a Zn starting material gas. This gas was heated up to 1,000° C. by a Zn starting material gas heater.

On the other hand, 25 Nm$^3$/hr of an oxidizing gas having a composition of 3 vol % water vapor and 97 vol % oxygen was heated by an oxidizing gas heater. The temperature of the heated gas was 1,030° C. at the inlet to a reactor.

Also, 700 g/hr of tetraethoxysilane was heated together with nitrogen up to 300° C. These Zn starting material gas, oxidizing gas and nitrogen gas containing tetraethoxysilane were introduced to a reactor.

The flow rate of the Zn starting material gas was 100 m/sec, the flow rate of the oxidizing gas was 90 m/sec and the flow rate of the nitrogen gas containing tetraethoxysilane was 40 m/sec. After the reaction, the powder was collected by a bag filter.

The obtained powder was white. The specific surface area thereof was measured by a BET one-point method using a monosorb-type apparatus manufactured by QUANTACH-ROME Co. Ltd. and found to be 42 m$^2$/g. Also, by the analysis using a fluorescent X-ray analyzer X-ray Spectrometer Simultix 10 manufactured by RIGAKU K.K., the powder was found to contain 4 mass % of silica component.

For examine the crystal form, this powder was scanned using an X-ray diffraction apparatus Model 2000/PC manufactured by RIGAKU K.K. under the conditions of 30 kV and 30 mA with a Cu-Kα line in the range of 2θ=10° to 80° at the rate of 2°/min.

As a result, this powder showed an XRD chart where peaks are present at 2θ=31.8°, 34.5° and 36.3° corresponding to the lattice faces (100), (002) and (101) peculiar to crystalline zinc oxide and a peak is also present in the vicinity of 2θ=22° corresponding to the lattice face (101) peculiar to crystalline silica.

Furthermore, in order to examine the heat resistance, the sample was split into a porcelain crucible, placed in an electric furnace at 800° C., kept for 1 hour and then, immediately taken out and cooled to room temperature. The specific surface area of this powder was again determined by the above-described BET one-point method. The specific surface area ratio before and after heating, namely, (specific surface area after heat treatment/specific surface area before heat treatment), was calculated and found to be 79%.

Primary particles observed by a transmission electron microscope (TEM) were classified into a tetrapod-like and needle-like anisotropic particles and isotropic particles and all particles on the TEM photograph were counted with an aim at counting 300 particles. As a result, the ratio of tetrapod-like and needle-form particles occupying in all particles was 83%.

Each primary particle of the tetrapod-like particle, the needle-like particle and the isotropic particle was subjected to elementary analysis in the measuring spot size of 5 nm by EDX, as a result, it was confirmed that Zn and Si are present in any shape particle. In each of the particles having these shapes, the elementary analysis was performed at a plurality of places, then, Zn and Si were detected in all places.

Production of Silica-Coated Mixed Crystal Oxide Particle 1

In a 50 L-volume reactor, 18.25 L of deionized water, 22.8 L of ethanol (produced by Junsei Kagaku K.K.) and 124 mL of 25 mass % aqueous ammonia (produced by Taisei Kako) were mixed. In this mixture, 1.74 kg of mixed crystal oxide particle produced in Production of Mixed Crystal Oxide Particle 1 was dispersed to prepare Suspension 1. Separately, 1.62 L of tetraethoxysilane (produced by GE Toshiba Silicone) and 1.26 L of ethanol were mixed to prepare Solution 1.

To Suspension 1 under stirring, Solution 1 was added at a constant rate over 9 hours. The resulting solution was ripened for 12 hours. The film formation and ripening were performed at 45° C. Thereafter, the solid content was separated by centrifugal filtration, vacuum dried at 50° C. for 12 hours, hot-air dried at 80° C. for 12 hours and ground in a jet mill to obtain Silica-Coated Mixed Crystal Oxide Particle 1.

Example 2

Production of Mixed Crystal Oxide Particle 2

To a zinc vaporizer, 6 kg/hr of metal zinc and 25 Nm$^3$/hr of nitrogen gas heated at 900° C. were supplied to obtain a Zn starting material gas. This gas was further heated up to 1,000° C. by a Zn starting material gas heater.

On the other hand, 25 Nm$^3$/hr of an oxidizing gas having a composition of 3 vol % water vapor and 97 vol % oxygen was heated by an oxidizing gas heater. The temperature of the heated gas was 1,030° C. at the inlet to a reactor.

Also, 10 kg/hr of tetraethoxysilane was heated together with nitrogen up to 300° C. These Zn starting material gas, oxidizing gas and nitrogen gas containing tetraethoxysilane were introduced to a reactor. The flow rate of the Zn starting material gas was 100 m/sec, the flow rate of the oxidizing gas was 90 m/sec and the flow rate of the nitrogen gas containing tetraethoxysilane was 50 m/sec. After the reaction, the powder was collected by a bag filter.

The obtained white powder was analyzed in the same manner as in Example 1. As a result, the specific surface area was 37 m$^2$/g and 26 mass % of silica component was contained. As for the crystal form, the powder had peaks at the same positions of 2θ as in Example 1. The specific surface area ratio before and after heating was 85%.

Production of Silica-Coated Mixed Crystal Oxide Particle 2

In a 50 L-volume reactor, 18.25 L of deionized water, 22.8 L of ethanol (produced by Junsei Kagaku K.K.) and 124 mL of 25 mass % aqueous ammonia (produced by Taisei Kako) were mixed. In this mixture, 1.96 kg of Mixed Crystal Oxide Particle 1 prepared above was dispersed to prepare Suspension 2. Separately, 0.81 L of tetraethoxysilane (produced by GE Toshiba Silicone) and 1.93 L of ethanol were mixed to prepare Solution 2.

To Suspension 2 under stirring, Solution 2 was added at a constant rate over 4.5 hours. The resulting solution was ripened for 12 hours. The film formation and ripening were performed at 45° C. Thereafter, the solid content was separated by centrifugal filtration, vacuum dried at 50° C. for 12 hours, hot-air dried at 80° C. for 12 hours and ground in a jet mill to obtain Silica-Coated Mixed Crystal Oxide Particle 2.

Example 3

Production of Mixed Crystal Oxide Particle 3

A gas containing 9.4 $Nm^3$/hr (N indicates the standard state, hereinafter the same) of gaseous titanium tetrachloride in a concentration of 100 vol % and a gas containing 2.4 $Nm^3$/hr of gaseous silicon tetrachloride in a concentration of 100 vol % were mixed. The resulting gas and a mixed gas containing 8 $Nm^3$/hr of oxygen and 20 $Nm^3$/hr of water vapor were each preheated at 1,000° C. and introduced into a reaction tube at a flow rate of 49 m/sec and 60 m/sec, respectively, using a coaxial parallel flow nozzle. The inner tube diameter of the coaxial parallel flow nozzle was 20 mm and a gas containing a mixed metal halide was introduced into the inner tube.

The inside diameter of the reaction tube was 100 mm, the flow rate inside the tube at a reaction temperature of 1,300° C. was 10 m/sec as a calculated value. After the reaction, a cooling air was introduced into the reaction tube such that the high-temperature residence time inside the reaction tube was 0.3 second or less. Thereafter, the ultrafine particle powder produced was collected using a Teflon®-made bag filter and then heated in an oven at 500° C. for 1 hour in an air atmosphere, thereby performing desalting.

The mixed crystal oxide particle obtained had a BET specific surface area of 88 $m^2$/g, an average true specific gravity of 3.7 g/ml, an average primary particle size of 0.018 µm and a chlorine content of 0.01% and by XPS (X-ray photoelectron spectroscopy), a titanium-oxygen-silicon bond was clearly confirmed.

The decrease percentage of the BET specific surface area after heating at 800° C. for 1 hour was 2%.

Production of Silica-Coated Mixed Crystal Oxide Particle 3

In a 50 L-volume reactor, 4.2 L of deionized water, 19.3 L of ethanol (produced by Junsei Kagaku K.K.) and 0.75 L of 25 mass % aqueous ammonia (produced by Taisei Kako) were mixed. In this mixture, 1.05 kg of Mixed Crystal Oxide Particle 3 prepared above was dispersed to prepare Suspension 3. Separately, 0.97 L of tetraethoxysilane (produced by GE Toshiba Silicone) and 1.05 L of ethanol were mixed to prepare Solution 3.

To Suspension 3 under stirring, Solution 3 was added at a constant rate over 6 hours. The resulting solution was ripened for 12 hours. The film formation and ripening were performed at 25° C. Thereafter, the solid content was separated by centrifugal filtration, vacuum dried at 50° C. for 12 hours, hot-air dried at 80° C. for 12 hours and ground in a jet mill to obtain Silica-Coated Mixed Crystal Oxide Particle 3.

Example 4

Production of Mixed Crystal Oxide Particle 4

A gas containing 8.3 $Nm^3$/hr of gaseous titanium tetrachloride, a gas containing 2.4 $Nm^3$/hr of gaseous aluminum trichloride and a gas containing 6 $Nm^3$/hr of nitrogen were mixed. The resulting gas and a mixed gas containing 8 $Nm^3$/hr of oxygen and 20 $Nm^3$/hr of water vapor were preheated at 900° C. and 1,000° C., respectively, and introduced into a reaction tube at a flow rate of 63 m/sec and 60 m/sec, respectively, using a coaxial parallel flow nozzle. The coaxial parallel flow nozzle had an inner tube diameter of 20 mm and a gas containing a mixed metal halide was introduced into the inner tube.

The inside diameter of the reaction tube was 100 mm and the flow rate inside the tube at a reaction temperature of 1,200° C. was 10 m/sec as a calculated value. After the reaction, a cooling air was introduced to the reaction tube such that the high temperature residence time inside the reactor was 0.3 second or less. Thereafter, the ultrafine particle powder produced was collected using a Teflon-made bag filter and then heated in an oven at 500° C. for 1 hour in an air atmosphere, thereby performing desalting.

The mixed crystal oxide particle obtained had a BET specific surface area of 48 $m^2$/g, an average true specific gravity of 3.9 g/cc, an average primary particle size of 0.032 µm and a chlorine content of 0.1% and by XPS, a titanium-oxygen-aluminum bond was clearly confirmed.

The decrease percentage of the BET specific surface area after heating at 800° C. for 1 hour was 5%.

Production of Silica-Coated Mixed Crystal Oxide Particle 4

In a 50 L-volume reactor, 4.2 L of deionized water, 19.3 L of ethanol (produced by Junsei Kagaku K.K.) and 0.75 L of 25 mass % aqueous ammonia (produced by Taisei Kako) were mixed. In this mixture, 1.05 kg of Mixed Crystal Oxide Particle 4 prepared above was dispersed to prepare Suspension 4. Separately, 0.44 L of tetraethoxysilane (produced by GE Toshiba Silicone) and 1.35 L of ethanol were mixed to prepare Solution 4.

To Suspension 4 under stirring, Solution 4 was added at a constant rate over 6 hours. The resulting solution was ripened for 12 hours. The film formation and ripening were performed at 25° C. Thereafter, the solid content was separated by centrifugal filtration, vacuum dried at 50° C. for 12 hours, hot-air dried at 80° C. for 12 hours and ground in a jet mill to obtain Silica-Coated Mixed Crystal Oxide Particle 4.

The silica-coated mixed crystal oxide particles obtained in Examples 1 to 4 were determined on the transmission infrared absorption spectrum by a KBr method. As a result, in any metal oxide particle, absorption originated from the Si—O—Si stretching vibration was observed at 1,000 to 1,200 $cm^{-1}$ and an absorption originated from the C—H stretching vibration was not observed at 2,800 to 3,000 $cm^{-1}$. From this, the coating formed was identified as silica.

Furthermore, the thickness of silica film, the ratio I of absorption peak intensities on the infrared absorption spectrum and the refractive index of silica film were measured. The results obtained are shown together in Table 1 below.

Measurement of Photocatalytic Activity, Tetralin Auto-Oxidation Method

The silica-coated mixed crystal oxide particles obtained in Examples 1 to 4 each was used as a test substance and measured on the photocatalytic activity by the tetralin auto-oxidation method. The results obtained are shown together in Table 1. In any of the silica-coated mixed crystal oxide particles of the present invention, the photocatalytic activity was 60 Pa/min or less, revealing inhibition of photocatalytic activity equal to that of conventional silica-coated metal oxide powders.

Measurement of Dye Discoloration Rate, Sunset Yellow Method

The silica-coated mixed crystal oxide particles obtained in Examples 1 to 4 each was used as a test substance and measured on the dye discoloration rate by the Sunset Yellow method. More specifically, Sunset Yellow as a dye for cosmetics was dissolved in 98 mass % glycerin to have a dye concentration of 0.02 mass %. Each test substance was dispersed therein to a concentration of 0.067 mass % and the resulting dispersion solution was irradiated with ultraviolet rays (ultraviolet intensity: 1.65 mW/cm$^2$). The absorbance at 490 nm which is the maximum absorption wavelength of Sunset Yellow was measured at an optical path length of 1 mm by a spectrophotometer (SHIMADZU UV-160) with the passage of time and the decrease rate of absorbance ($\Delta A_{490}$/hr) was calculated. The results are shown in Table 1.

In any of the silica-coated mixed crystal oxide particles for use in the present invention, the dye discoloration rate was 0.10 ($\Delta A_{490}$/hr) or less, revealing a dye discoloration rate equal to that of conventional silica-coated metal oxide powders. The silica-coated mixed crystal oxide particle of the present invention maintains the low dye decomposing property of conventional silica-coated metal oxide powders and can provide a cosmetic material having high storage stability.

In a tetralin auto-oxidation method, tetralin is oxidized by the irradiation of tetralin itself by ultraviolet light, and tetralin is also subjected to oxidative decomposition by active oxygen which is generated in the system of measurement due to photocatalytic activity of a compound present, such as titanium oxide or zinc oxide. Therefore, even if titanium oxide or zinc oxide is not present, tetralin is decomposed only by the irradiation by ultraviolet light.

In addition, in a system in which titanium oxide or zinc oxide is present, the oxidation rate is determined as a result of a concerted effect of both ultraviolet-shielding capability and photocatalytic activity. Although a lower oxidation rate means a higher ultraviolet-shielding capability and a lower photocatalytic activity, contribution of each to the oxidation rate is unknown.

On the other hand, in a measurement of a dye discoloration rate by a Sunset Yellow method, almost no dye, Sunset Yellow, is decomposed and discolored only by the irradiation by ultraviolet light. Therefore, in a system to which a compound having photocatalytic activity such as titanium oxide or zinc oxide is added, decomposition (discoloration) of the dye due to the photocatalytic activity can be detected.

Measurement of Decomposition Rate of Organic Ultraviolet Absorber, Parsol Method The silica-coated mixed crystal oxide particles obtained in Examples 1 to 4 each was used as a test substance and measured on the decomposition rate of organic ultraviolet absorber by the Parsol method. More specifically, each test substance was dispersed in a polyethylene glycol 300 solution (0.045 mass % as a Parsol 1789 concentration) of 4-tert-butyl-4'-methoxydibenzoylmethane (Parsol 1789) to form a slurry having a solid content of 1 mass %. Then, 1.5 g of the slurry was charged into a glass vessel and irradiated with ultraviolet rays (1.65 mW/cm$^2$). Thereafter, 1 g was split and thereto, 2 mL of isopropyl alcohol, 2 mL of hexane and 3 mL of distilled water were sequentially added.

The resulting solution was stirred to extract Parsol 1789 in the hexane phase and the absorbance (at 340 nm) of the hexane phase at an optical path length of 1 mm was measured by a spectrophotometer (SHIMADZU UV-160) with the passage of time (at 3 points, i.e., 0, 5 or 10 hours after the irradiation of ultraviolet rays). From the values obtained, the decrease rate of absorbance at 340 nm ($\Delta A_{340}$/hr) was determined. The results are shown together in Table 1.

In any of the silica-coated mixed crystal oxide particles which can be used in the present invention, the decrease rate was 0.01 ($\Delta A_{340}$/hr) or less and thus, the decomposing property of organic ultraviolet absorber was low. Accordingly, the cosmetic material containing the silica-coated mixed crystal oxide particle can be used in combination with an organic ultraviolet-shielding material and can maintain the capability of ultraviolet protection for a long period of time.

Measurement of Powder Kinetic Friction Coefficient, Glass Plate Method

The silica-coated mixed crystal oxide particles obtained in Examples 1 to 4 each was used as a test substance and measured on the powder kinetic friction coefficient by the glass plate method. More specifically, the powder as a test substance was dispersed on a glass plate of 100×200 mm to a coverage of 10 mg/cm$^2$. This glass plate was placed on the test table of a surface property measuring apparatus (HEIDON) and the coefficient of kinetic friction was measured under conditions such that the load was 22.2 g/cm$^2$, the moving speed was 200 mm/min and the moving distance was 20 mm. The results are shown in Table 1.

TABLE 1

Physical Properties of Silica-Coated Mixed Crystal Oxide

| | Example 1 | Example 2 | Example 3 | Example 4 |
|---|---|---|---|---|
| Film thickness (nm) | 3 | 1.5 | 1.1 | 1 |
| I Value | 0.5 | 0.5 | 0.45 | 0.4 |
| Refractive index | 1.45 | 1.445 | 1.442 | 1.44 |
| Tetralin activity (Pa/min) | 40 | 38 | 52 | 45 |
| Dye discoloration rate ($\Delta A_{490}$/hr) | 0 | 0 | 0.09 | 0.06 |
| Parsol decomposition rate ($\Delta A_{340}$/hr) | 0.003 | 0.002 | 0.017 | 0.015 |
| Powder kinetic friction coefficient | 0.48 | 0.45 | 0.52 | 0.49 |

In any of the silica-coated mixed crystal oxide particles of the present invention, the powder kinetic friction coefficient was 0.550 or less, thus, a powder kinetic friction coefficient further lower than that of conventional silica-coated metal oxide powders was revealed. This suggests that the cosmetic material containing the silica-coated mixed crystal oxide particle of the present invention has still more excellent use feeling than conventional cosmetic materials.

Examples 5 to 8

Sunscreen Milky Lotion

Sunscreen milky lotions having the following formulation were produced by an ordinary method. More specifically, polyethylene glycol was added to purified water and dissolved under heating. Thereto, a test substance and bee gum were added, uniformly dispersed by a homomixer and kept at 70° C. (aqueous phase). Remaining ingredients were mixed, dissolved under heating and kept at 70° C. (oil phase). The oil phase was added to the aqueous phase and uniformly emulsion-dispersed using a homomixer. After the emulsification, the emulsified product was cooled to 35° C. while stirring. As a test substance, the silica-coated mixed crystal oxide particles produced in Examples 1 to 4 were used. For dispersing the silica-coated mixed crystal oxide particle in the oil phase side of the milky lotion, the particle was subjected to a treatment for rendering the surface hydrophobic before use such that dimethylpolysiloxane became 3 mass % based on the weight of the treated powder (hereinafter, this hydrophobitized product is called a "silicone-treated silica-coated mixed crystal oxide particle").

| Formulation of Sunscreen Milky Lotion: | |
| --- | --- |
| Silicone-treated silica-coated mixed crystal oxide particle | 7.0 mass % |
| Stearic acid | 2.0 mass % |
| Cetyl alcohol | 1.0 mass % |
| Petrolatum | 5.0 mass % |
| Silicone oil | 2.0 mass % |
| Liquid paraffin | 10.0 mass % |
| Glycerol monostearate (self-emulsifying) | 1.0 mass % |
| Polyoxyethylene (25 mol) monooleate | 1.0 mass % |
| Polyethylene glycol 1500 | 5.0 mass % |
| Bee gum | 0.5 mass % |
| Purified water | 65.2 mass % |
| Perfume | 0.1 mass % |
| Antiseptic | 0.2 mass % |

As Comparative Examples, sunscreen milky lotions were prepared using conventional surface-treated titanium oxide (TTO-S-1, produced by Ishihara Sangyo Kaisha, Ltd.) or conventional zinc oxide (ZnO 350, produced by Sumitomo Osaka Cement Corp.) in place of the silica-coated mixed crystal oxide particle (Comparative Examples 1 and 2).

Furthermore, a sunscreen milky lotion of Comparative Example 3 was prepared using a silica-coated zinc oxide obtained by using zinc oxide (UFZ 40, produced by Showa Titanium Co., Ltd.) in place of Mixed Crystal Oxide Particle 1 in Silica-Coated Mixed Crystal Oxide Particle 1 of Example 1, and a sunscreen milky lotion of Comparative Example 4 was prepared using a silica-coated titanium oxide obtained by using titanium oxide (F4, produced by Showa Titanium Co., Ltd.) in place of Mixed Crystal Oxide Particle 4 in Silica-Coated Mixed Crystal Oxide Particle 4 of Example 4 (sensory test).

The sunscreen milky lotions produced in Examples 5 to 8 and Comparative Examples 1 to 4 were evaluated on the use feeling and the finish transparency by a sensory test using 50 women in their twenties to forties. The use feeling of each foundation was rated by 50 subjects according to the following criteria:
very good: 5 points, good: 3 points, normal: 2 points, bad: 1 point, and very bad: 0 point.

The evaluation points by 50 subjects were totaled and the use feeling was judged in 5 grades by the totaled points according to the following criteria:

| | | |
| --- | --- | --- |
| 200 to 250 points: | very good | (++) |
| 150 to 200 points: | good | (+) |
| 100 to 150 points: | normal | (+−) |
| 50 to 100 points: | bad | (−) |
| 0 to 50 points: | very bad | (−−) |

The results are shown in Table 2.

TABLE 2

Sensory Test Results

| | | Judgment | |
| --- | --- | --- | --- |
| Specimen | Mixed Crystal Oxide Used | Use Feeling | Transparency |
| Example 5 | Example 1 | ++ | ++ |
| Example 6 | Example 2 | ++ | ++ |
| Example 7 | Example 3 | ++ | ++ |
| Example 8 | Example 4 | ++ | ++ |
| Comparative Example 1 | TTO-S-1, produced by Ishihara Sangyo | − | − |
| Comparative Example 2 | ZnO 350, produced by Sumitomo Osaka Cement | − | +− |
| Comparative Example 3 | silica-coated zinc oxide | ++ | + |
| Comparative Example 4 | silica-coated titanium oxide | ++ | +− |

The sunscreen milky lotions having blended therein the silica-coated mixed crystal oxide particle of the present invention all were graded very good (++) on the use feeling and the transparency.

It is apparent that the sunscreen milky lotion containing the silica-coated mixed crystal oxide particle of the present invention is improved particularly in the transparency.

Examples 9 to 12

Foundation

Foundations having the following formulation were produced by an ordinary method. Test substances used were the silica-coated mixed crystal oxide particles obtained in Examples 1 to 4.

| Formulation of Foundation: | |
| --- | --- |
| Silica-coated mixed crystal oxide particle | 15.0 mass % |
| Mica | 15.0 mass % |
| Talc | 10.0 mass % |
| Zinc white | 15.0 mass % |
| Iron oxide (red) | 1.5 mass % |
| Iron oxide (yellow) | 3.4 mass % |
| Glycerin | 10.0 mass % |
| Purified water | 30.0 mass % |
| Perfume | 0.1 mass % |

As Comparative Examples, foundations were prepared using conventional surface-treated titanium oxides (TTO-S-1, produced by Ishihara Sangyo Kaisha, Ltd.) or conventional zinc oxide (ZnO 350, produced by Sumitomo Osaka Cement Corp.) in place of the silica-coated mixed crystal oxide particle (Comparative Examples 5 and 6).

Furthermore, a foundation of Comparative Example 7 was prepared using silica-coated zinc oxide obtained by using zinc oxide (UFZ 40, produced by Showa Titanium Co., Ltd.) in place of Mixed Crystal Oxide Particle 1 in Silica-Coated Mixed Crystal Oxide Particle 1 of Example 1.

Also, a foundation of Comparative Example 8 was prepared using silica-coated titanium oxide obtained by using titanium oxide (F4, produced by Showa Titanium Co., Ltd.) in place of Mixed Crystal Oxide Particle 4 in Silica-Coated Mixed Crystal Oxide Particle 4 of Example 4.

(Sensory Test)

The foundations produced in Examples 9 to 12 were evaluated on the use feeling and the finish transparency by a sensory test according to the above-described method.

The results are shown in the Table 3.

TABLE 3

Sensory Test Results

| Specimen | Mixed Crystal Oxide Used | Judgment | |
|---|---|---|---|
| | | Use Feeling | Transparency |
| Example 9 | Example 1 | ++ | ++ |
| Example 10 | Example 2 | ++ | ++ |
| Example 11 | Example 3 | ++ | ++ |
| Example 12 | Example 4 | ++ | ++ |
| Comparative Example 5 | TTO-S-1, produced by Ishihara Sangyo | − | − |
| Comparative Example 6 | ZnO 350, produced by Sumitomo Osaka Cement | − | +− |
| Comparative Example 7 | silica-coated zinc oxide | ++ | + |
| Comparative Example 8 | silica-coated titanium oxide | ++ | +− |

The foundations having blended therein the silica-coated mixed crystal oxide particles of the present invention all were graded very good (++) on the use feeling and the transparency.

It is apparent that the foundation containing the silica-coated mixed crystal oxide particles of the present invention is improved particularly in the transparency.

Example 13

Skin Lotion

A skin lotion having the following formulation was produced by an ordinary method.

| Formulation of Skin Lotion: | |
|---|---|
| Silica-coated mixed crystal oxide particle 1 | 3.0 mass % |
| Ethyl alcohol | 39.6 mass % |
| 1,3-Butylene glycol | 9.5 mass % |
| Castor oil | 4.9 mass % |
| Methylparaben | 0.2 mass % |
| Purified water | 42.8 mass % |

This lotion was subjected to a sensory test, as a result, rated to give good use feeling and very good transparency.

Example 14

Milky Lotion

A milky lotion having the following formulation was produced by an ordinary method.

| Formulation of Milky Lotion: | |
|---|---|
| Silicone-treated silica-coated mixed crystal oxide particle | 3.0 mass % |
| Avocado oil | 11.0 mass % |
| Behenyl alcohol | 0.6 mass % |
| Stearic acid | 0.4 mass % |
| Glycerin fatty acid ester | 0.9 mass % |
| Polyoxyethylene sorbitan fatty acid ester | 1.1 mass % |
| Polyoxyethylene alkyl ether | 0.4 mass % |
| 1,3-Butylene glycol | 10.1 mass % |
| Methylparaben | 0.2 mass % |
| Perfume | 0.4 mass % |
| Purified water | 71.9 mass % |

This lotion was subjected to a sensory test, as a result, rated to give very good use feeling and very good transparency.

Example 15

Cream

A cream having the following formulation was produced by an ordinary method.

| Formulation of Cream: | |
|---|---|
| Silicone-treated silica-coated mixed crystal oxide particle 1 | 3.5 mass % |
| Squalane | 15.2 mass % |
| Stearic acid | 7.8 mass % |
| Stearyl alcohol | 6.0 mass % |
| Beeswax | 1.9 mass % |
| Propylene glycol monostearate | 3.1 mass % |
| Polyoxyethylene cetyl ether | 1.1 mass % |
| 1,3-Butylene glycol | 11.9 mass % |
| Methylparaben | 0.2 mass % |
| Perfume | 0.4 mass % |
| Purified water | 41.9 mass % |

This cream was subjected to a sensory test, as a result, rated to give very good use feeling and very good transparency.

Example 16

Pack

A pack was produced according to the following formulation by an ordinary method using the silica-coated mixed crystal oxide particle obtained in Example 3 as a test substance.

| Formulation of Pack: | |
|---|---|
| Silica-coated mixed crystal oxide particle 3 | 7.0 mass % |
| Polyvinyl alcohol | 14.5 mass % |

| Formulation of Pack: | |
|---|---|
| Sodium carboxymethylcellulose | 4.8 mass % |
| 1,3-Butylene glycol | 2.9 mass % |
| Ethyl alcohol | 10.0 mass % |
| Methylparaben | 0.1 mass % |
| Purified water | 60.7 mass % |

This pack was subjected to a sensory test, as a result, rated to give good use feeling and good transparency.

Example 17

Lipstick

A lipstick was produced according to the following formulation by an ordinary method using the silica-coated mixed crystal oxide particle (before use, subjected to a treatment for rendering the surface hydrophobic such that dimethylpolysiloxane became 3 mass % based on the weight of the treated powder) of Example 1 as a test substance.

| | |
|---|---|
| Silicone-treated silica-coated mixed crystal oxide particle 1 | 3.0 mass % |
| Silicone oil | 27.0 mass % |
| Castor oil | 18.3 mass % |
| Hexadecyl alcohol | 25.2 mass % |
| Lanolin | 3.9 mass % |
| Beeswax | 4.8 mass % |
| Ozokerite | 3.4 mass % |
| Candelilla wax | 6.2 mass % |
| Carnauba wax | 2.1 mass % |
| Methylparaben | 0.1 mass % |
| Red dye | 4.8 mass % |
| Perfume | 0.1 mass % |
| Purified water | 1.1 mass % |

This lipstick was subjected to a sensory test, as a result, rated to give very good use feeling and good transparency.

Examples 18 to 21

Two-Way Foundation

Two-way foundations (Example 18 to 21) were produced according to the following formulation by an ordinary method using the silica-coated mixed crystal oxide particle (before use, subjected to a treatment for rendering the surface hydrophobic such that dimethylpolysiloxane became 3 mass % based on the weight of the treated powder) obtained in Examples 1 to 4 as a test substance.

| Formulation of Two-Way Foundation: | |
|---|---|
| Silicone-treated silica-coated mixed crystal oxide particle | 6.0 mass % |
| Silicone-treated talc | 19.0 mass % |
| Silicone-treated mica | 39.6 mass % |
| Silicone-treated iron oxide (red) | 1.0 mass % |
| Silicone-treated iron oxide (yellow) | 3.0 mass % |
| Silicone-treated iron oxide (black) | 0.3 mass % |
| Silicone-treated titania | 15.0 mass % |
| Zinc stearate | 0.2 mass % |
| Nylon powder | 2.0 mass % |
| Squalane | 4.0 mass % |
| Solid paraffin | 0.5 mass % |

| Formulation of Two-Way Foundation: | |
|---|---|
| Dimethylpolysiloxane | 4.0 mass % |
| Glycerol triisooctanoate | 5.0 mass % |
| Antioxidant | 0.2 mass % |
| Antiseptic | 0.1 mass % |
| Perfume | 0.1 mass % |

The two-way foundations in Examples 18 to 21 were subjected to a sensory test and evaluated on the use feeling and the transparency. The foundations containing the silica-coated mixed crystal oxide particle of the present invention all exhibited very good use feeling and very good transparency.

Examples 22 to 25

W/O Sunscreen Cream

W/O Sunscreen creams (Examples 22 to 25) having the following formulation were produced using the silica-coated mixed crystal oxide particles (before use, subjected to a treatment for rendering the surface hydrophobic such that dimethylpolysiloxane became 3 mass % based on the weight of the treated powder) obtained in Examples 1 to 4 as a test substance.

(1) 12.0 mass % of glyceryl 2-ethylhexanoate, (2) 5.0 mass % of 4-tert-butyl-4'-methoxydibenzoylmethane, (3) 1.0 mass % of polyglyceryl isostearate, (4) 2.0 mass % of sorbitan sesquioleate, (5) 10.0 mass % of decamethylpolysiloxane, (6) 0.2 mass % of organic denatured bentonite, (7) 5.0 mass % of squalane, (8) 8.0 mass % of 2-ethylhexyl paramethoxycinnamate, (9) 10.0 mass % of silicone-treated silica-coated mixed crystal oxide particle, (10) 0.1 mass % of perfume, (11) 0.3 mass % of methyl parahydroxybenzoate, (12) 0.1 mass % of disodium edetate, and (13) 46.3 mass % of purified water.

(1) to (8) were dissolved under heating, (9) and (10) were added thereto and uniformly dispersed, and (11) to (13) were gradually added, thereby performing the emulsification. After thorough stirring, the emulsified product was cooled to 30° C. to obtain a W/O sunscreen cream.

Examples 26 to 29

O/W Sunscreen Cream

O/W Sunscreen creams (Examples 26 to 29) having the following formulation were produced using the silica-coated mixed crystal oxide particles (before use, subjected to a treatment for rendering the surface hydrophobic such that dimethylpolysiloxane became 3 mass % based on the weight of the treated powder) obtained in Examples 1 to 4 as a test substance.

(1) 5.0 mass % of squalane, (2) 10.0 mass % of glyceryl 2-ethylhexanoate, (3) 1.0 mass % of microcrystalline wax, (4) 2.0 mass % of stearyl alcohol (5) 0.1 mass % of butyl parahydroxybenzoate, (6) 1.0 mass % of 4-tert-butyl-4'-methoxydibenzoylmethane, (7) 3.0 mass % of 2-ethylhexyl paramethoxycinnamate, (8) 5.0 mass % of silicone-treated silica-coated mixed crystal oxide particle, (9) 0.2 mass % of perfume, (10) 0.1 mass % of methyl parahydroxybenzoate, (11) 7.0 mass % of 1,3-butylene glycol, and (12) 65.6 mass % of purified water.

(1) to (7) were dissolved under heating, (8) and (9) were added thereto and uniformly dispersed, and (10) to (12) were gradually added, thereby performing the emulsification. After thorough stirring, the emulsified product was cooled to 30° C. to obtain an O/W sunscreen cream.

Examples 30 to 33

Lipstick

Lipsticks (Examples 30 to 33) having the following formulation were produced using the silica-coated mixed crystal oxide particles (before use, subjected to a treatment for rendering the surface hydrophobic such that dimethylpolysiloxane became 3 mass % based on the weight of the treated powder) obtained in Examples 1 to 4 as a test substance.

(1) 10.0 mass % of paraffin wax, (2) 10.0 mass % of microcrystalline wax, (3) 3.0 mass % of silicone-treated silica-coated mixed crystal oxide particle, (4) 46.4 mass % of glyceryl 2-ethylhexanoate, (5) 5.0 mass % of 2-ethylhexyl paramethoxycinnamate, (6) 3.0 mass % of 4-tert-butyl-4'-methoxydibenzoylmethane, (7) 15.0 mass % of diisostearyl malate, (8) 2.0 mass % of Food Red 201, (9) 2.0 mass % of Food Red 202, (10) 0.5 mass % of Food Blue 1, (11) 3.0 mass % of red iron oxide, and (12) 0.1 mass % of perfume.

(1) to (11) were dissolved under heating, (12) was added thereto and uniformly dispersed, and the resulting dispersion was cooled to 30° C. to obtain a lipstick.

Examples 34 to 37

Powder Foundation

Powder foundations (Examples 34 to 37) having the following formulation were produced using the silica-coated mixed crystal oxide particles obtained in Examples 1 to 4 as a test substance.

(1) 36.0 mass % of mica, (2) 20.0 mass % of talc, (3) 6.0 mass % of silica-coated mixed crystal oxide particle, (4) 5.0 mass % of 2-ethylhexyl paramethoxycinnamate, (5) 10.0 mass % of 4-tert-butyl-4'-methoxydibenzoylmethane, (6) 4.0 mass % of zinc stearate, (7) 3.0 mass % of yellow iron oxide, (8) 0.8 mass % of red iron oxide, (9) 0.2 mass % of black iron oxide, (10) 5.0 mass % of squalane, (11) 8.7 mass % of glyceryl 2-ethylhexanoate, (12) 1.0 mass % of sorbitan monoisostearate, (13) 0.2 mass % of butyl p-hydroxybenzoate, and (14) 0.1 mass % of perfume.

(10) to (13) were dissolved under heating and then (14) was mixed thereto. The resulting mixture was cooled to room temperature to prepare the oil phase. (1) to (9) were thoroughly stirred by a mixer and the oil phase was added thereto and sufficiently mixed. This resulting mixture was passed through a pulverizer and the pulverized product was pressed on a metal plate to obtain an objective powder foundation.

Cosmetic materials of Comparative Examples were prepared by changing the silica-coated mixed crystal oxide particle in the formulation of Examples 34 to 37 to a conventional surface-treated titanium oxide (TTO-S-1, produced by Ishihara Sangyo Kaisha, Ltd.) or a conventional zinc oxide (ZnO 350, produced by Sumitomo Osaka Cement Corp.) and judged on the aging stability after one month with an eye.

In all of Comparative Examples, precipitation of 4-tert-butyl-4'-methoxydibenzoylmethane was observed, whereas the cosmetic materials having blended thereto the silica-coated mixed crystal oxide particle of Examples 34 to 37 all were free from precipitation of 4-tert-butyl-4'-methoxydibenzoylmethane and exhibited excellent aging stability.

The cosmetic materials obtained in Examples 34 to 37 exhibited excellent aging stability and excellent temperature stability. That is, the cosmetic materials of the present invention are remarkably improved in the aging stability as compared with conventional cosmetic materials having blended therein 4-tert-butyl-4'-methoxydibenzoylmethane and can be suitably used in various perfumes and cosmetic materials.

INDUSTRIAL APPLICABILITY

According to the present invention, a silica-coated mixed crystal oxide particle covered with a dense and practical silica film and improved in dispersibility and transparency, and a profitable production process thereof are provided. Furthermore, an ultraviolet-shielding cosmetic material having good dispersion of silica-coated mixed crystal oxide particles and, in particular, having high transparency and excellent storage stability is provided.

The invention claimed is:

1. A silica-coated mixed crystal oxide particle, comprising:
 a mixed crystal oxide particle having a BET specific surface area of 10 to 200 $m^2/g$ and containing primary particles in a mixed crystal; and
 a dense and thin silica film covering a surface of the mixed crystal oxide particle,
 wherein the mixed crystal oxide particle contains zinc oxide crystals and silica crystals in the primary particle.

2. The silica-coated mixed crystal oxide particle according to claim 1, wherein a thickness of the silica film is from 0.1 to 25 nm.

3. The silica-coated mixed crystal oxide particle according to claim 1 or 2, wherein a photocatalytic activity determined by a tetralin auto-oxidation method is 60 Pa/mm or less.

4. The silica-coated mixed crystal oxide particle according to claim 1, wherein the silica film has a ratio I of an absorption peak intensity of 1,150 to 1,250 $cm^{-1}$ to an absorption peak intensity of 1,000 to 1,100 $cm^{-1}$ on an infrared absorption spectrum ($I=I_1/I_2$, wherein $I_1$ represents a maximum absorption peak intensity in a range of 1,150 to 1,250 $cm^{-1}$ and $I_2$ represents a maximum absorption peak intensity in a range of 1,000 to 1,100 $cm^{-1}$) of 0.2 or more and a refractive index of 1,435 or more.

5. The silica-coated mixed crystal oxide particle according claim 1, wherein a dye discoloration rate ($\Delta ABS_{490}/hr$) determined by a Sunset Yellow method is 0.1 or less.

6. The silica-coated mixed crystal oxide particle according to claim 1, wherein a kinetic friction coefficient determined by a glass plate method is 0.55 or less.

7. The silica-coated mixed crystal oxide particle according to claim 1, wherein the mixed crystal oxide particle is a composite oxide containing zinc oxide crystals and silica crystals, having diffraction peaks on lattice faces (100), (002), and (101) which are diffraction peaks peculiar to crystalline zinc oxide in view of X-ray crystallography, and on lattice face (101) which is a diffraction peak peculiar to crystalline silica, and mainly comprising zinc oxide.

8. The silica-coated mixed crystal oxide particle according to claim 7, wherein the mixed crystal oxide particle is a mixed crystal oxide particle containing a mixed crystal having a zinc-oxygen-silicon bond inside the primary particle.

9. The silica-coated mixed crystal oxide particle according to claim 7, wherein the mixed crystal oxide particle is a composite oxide produced by a vapor phase reaction of oxidizing a gaseous zinc in the presence of oxygen and water vapor and in the vapor phase reaction, a Zn starting material gas containing a gaseous zinc in an inert gas, and an oxidizing gas containing oxygen and water vapor are each introduced into a reactor to allow the oxidation reaction of zinc to proceed inside the reactor and a silicon-containing composition is introduced into this reaction zone and oxidized.

10. The silica-coated mixed crystal oxide particle according to claim 1, wherein a decrease in percentage of the BET specific surface area after heating at 800° C. for 1 hour is 30% or less.

11. The silica-coated mixed crystal oxide particle according to claim 1, wherein-the a surface of the silica film is hydrophobized with a hydrophobicity-imparting agent.

12. The silica-coated mixed crystal oxide particle according to claim 11, wherein the hydrophobicity-imparting agent is one or more selected from the group consisting of silicone oils, alkoxysilanes, silane coupling agents and higher fatty acid salts.

13. A production process for the silica-coated mixed crystal oxide particle according to claim 1, comprising adding, in any order, a) a mixed crystal oxide particle having a BET specific surface area of 10 to 200 $m^2/g$ and containing primary particles in a mixed crystal in which zinc oxide crystals and silica crystals are contained in the primary particle, b) a silicic acid containing neither an organic group nor a halogen or a precursor capable of producing the silicic acid, c) an alkali, d) an organic solvent and e) water such that the water/organic solvent ratio after the addition is from 0.1 to 10 and a silicon concentration is from 0.0001 to 5 mol/liter, thereby selectively forming a dense silica thin film on the surface of the mixed crystal oxide particle.

14. The production process according to claim 13, comprising adding a) the mixed crystal oxide particle having a BET specific surface area of 10 to 200 $m^2/g$ and containing primary particles in a mixed crystal state to a mixed solution of c) the alkali, d) the organic solvent and e) the water, and further adding a mixed solution of b) the silicic acid containing neither an organic group nor a halogens or a precursor capable of producing the silicic acid, and either of f) an organic solvent or a mixture of f) the organic solvent and g) water such that the water/organic solvent ratio after the addition is from 0.1 to 10 and a silicon concentration is from 0.000 1 to 5 mol/liter, thereby selectively forming a dense silica thin film on the surface of the mixed crystal oxide particle.

15. The production process according to claim 13 or 14, wherein the alkali is one or more selected from the group consisting of ammonia, ammonium carbonate, ammonium hydrogencarbonate, ammonium formate and ammonium acetate.

16. The production process according to claim 13 or 14, wherein the organic solvent is one or more selected from the group consisting of methanol, ethanol, propanol, pentanol, tetrahydrofuran, 1,4-dioxane and acetone.

17. A silica-coated mixed crystal oxide particle produced by the production process according to claim 13 or 14,
wherein the mixed crystal oxide particle contains zinc oxide crystals and silica crystals in the primary particle.

18. A cosmetic material comprising the silica-coated mixed crystal oxide particle according to claim 1.

19. The cosmetic material according to claim 18, which comprises an antioxidant.

20. The cosmetic material according to claim 18, which comprises an organic ultraviolet absorber.

21. An The cosmetic material according to claim 18, which is used for an ultraviolet-protecting cosmetic preparation.

22. The cosmetic material according to claim 21, which is a W/O or O/W milky lotion, a cream, a foundations or a gel.

23. A cosmetic material comprising the silica-coated mixed crystal oxide particle according to claim 17.

24. The cosmetic material according to claim 23, which comprises an antioxidant.

25. The cosmetic material according to claim 23, which comprises an organic ultraviolet absorber.

26. An The cosmetic material according to claim 23, which is used for an ultraviolet-protecting cosmetic preparation.

27. The cosmetic material according to claim 26, which is a W/O or O/W milky lotion, a cream, a foundations or a gel.

* * * * *